(12) United States Patent
Wulfman et al.

(10) Patent No.: US 6,818,001 B2
(45) Date of Patent: Nov. 16, 2004

(54) INTRALUMENAL MATERIAL REMOVAL SYSTEMS AND METHODS

(75) Inventors: Edward I. Wulfman, Woodinville, WA (US); Thomas J. Clement, Redmond, WA (US); Craig E. Lawson, Redmond, WA (US); David C. Auth, Kirkland, WA (US)

(73) Assignee: Pathway Medical Technologies, Inc.

( * ) Notice: Subject to any disclaimer, the term of this patent is extended or adjusted under 35 U.S.C. 154(b) by 472 days.

(21) Appl. No.: 09/826,487

(22) Filed: Apr. 4, 2001

(65) Prior Publication Data

US 2002/0007190 A1 Jan. 17, 2002

Related U.S. Application Data

(63) Continuation-in-part of application No. 09/724,914, filed on Nov. 28, 2000.
(60) Provisional application No. 60/194,805, filed on Apr. 5, 2000, provisional application No. 60/194,998, filed on Apr. 5, 2000, and provisional application No. 60/194,952, filed on Apr. 5, 2000.

(51) Int. Cl.$^7$ .............................................. A61B 17/32

(52) U.S. Cl. ...................... 606/159; 606/167; 606/170; 606/171; 606/180

(58) Field of Search ................................ 606/167, 170, 606/180, 1, 108, 159, 171; 604/22

(56) References Cited

U.S. PATENT DOCUMENTS

| | | |
|---|---|---|
| 3,854,916 A | 12/1974 | Dochterman |
| 4,445,509 A | 5/1984 | Auth .......................... 128/305 |
| 4,631,052 A | 12/1986 | Kensey ........................ 604/22 |
| 4,679,557 A | 7/1987 | Opie et al. |
| 4,700,705 A | 10/1987 | Kensey et al. .............. 128/341 |
| 4,747,821 A | 5/1988 | Kensey et al. ................ 604/22 |
| 4,886,061 A | 12/1989 | Fischell et al. ............. 128/305 |
| 4,895,560 A | 1/1990 | Papantonakos ............... 604/22 |
| 4,926,858 A * | 5/1990 | Gifford et al. .............. 606/159 |
| 4,966,604 A | 10/1990 | Reiss .......................... 606/159 |
| 4,990,134 A | 2/1991 | Auth ........................... 604/22 |
| 5,002,553 A | 3/1991 | Shiber ........................ 606/159 |
| 5,030,201 A | 7/1991 | Palestrant ................... 604/22 |
| 5,042,984 A | 8/1991 | Kensey et al. .............. 606/128 |
| 5,097,849 A | 3/1992 | Kensey et al. .............. 128/898 |
| 5,100,425 A | 3/1992 | Fischell et al. ............. 606/159 |
| 5,152,773 A | 10/1992 | Redha ......................... 606/159 |
| 5,154,724 A | 10/1992 | Andrews ..................... 606/159 |
| 5,158,564 A | 10/1992 | Schnepp-Pesch et al. ... 606/159 |
| 5,176,693 A | 1/1993 | Pannek, Jr. .................. 606/159 |
| 5,192,291 A | 3/1993 | Pannek, Jr. .................. 606/159 |
| 5,217,474 A | 6/1993 | Zacca et al. ................ 606/159 |
| 5,224,945 A | 7/1993 | Pannek, Jr. .................. 606/159 |
| 5,234,451 A | 8/1993 | Osypka |
| 5,282,813 A | 2/1994 | Redha ......................... 606/159 |
| 5,308,354 A | 5/1994 | Zacca et al. ................ 606/159 |

(List continued on next page.)

Primary Examiner—Henry P. Bennett
Assistant Examiner—Kathryn Odland
(74) Attorney, Agent, or Firm—Ann W. Speckman; Janet Sleath; Lisa N. Benado

(57) ABSTRACT

The intralumenal material removal system includes a cutter assembly positionable in the lumen of a mammalian subject and operably connected to system controls. The cutter assembly is axially advanceable by translating the drive shaft and rotatable by rotating the drive shaft. One cutter assembly comprises an adjustable cutter that is adjustable between a smaller diameter condition and a larger diameter condition by rotation of the drive shaft in opposite directions. The cutter may thus be introduced to and withdrawn from the material removal site in a retracted, smaller diameter condition that facilitates translation and navigation of the device through various lumens. The adjustable cutting assembly may be selectively expanded at the material removal site to facilitate cutting, removal and aspiration of the occlusive material. One composite cutter assembly comprises both a distal, fixed diameter cutter and a proximal adjustable diameter cutter.

27 Claims, 20 Drawing Sheets

U.S. PATENT DOCUMENTS

| | | | |
|---|---|---|---|
| 5,314,407 A | 5/1994 | Auth et al. | 604/22 |
| 5,395,311 A | 3/1995 | Andrews | 604/22 |
| 5,417,703 A | 5/1995 | Brown et al. | 606/159 |
| 5,419,774 A | 5/1995 | Willard et al. | 604/22 |
| 5,423,754 A | 6/1995 | Cornelius et al. | 604/103 |
| 5,490,859 A | 2/1996 | Mische et al. | 606/159 |
| 5,540,707 A | 7/1996 | Ressemann et al. | 606/159 |
| 5,556,408 A | 9/1996 | Farhat | 606/180 |
| 5,584,843 A * | 12/1996 | Wulfman et al. | 606/159 |
| 5,609,602 A | 3/1997 | Machemer et al. | |
| 5,667,490 A | 9/1997 | Keith et al. | 604/22 |
| 5,681,336 A * | 10/1997 | Clement et al. | 606/159 |
| 5,695,507 A | 12/1997 | Auth et al. | 606/159 |
| RE35,787 E | 5/1998 | Nash et al. | 606/128 |
| 5,766,190 A | 6/1998 | Wulfman | 606/159 |
| 5,766,192 A | 6/1998 | Zacca | 606/159 |
| 5,792,157 A | 8/1998 | Mische et al. | 606/159 |
| 5,836,868 A | 11/1998 | Ressemann et al. | 606/159 |
| 5,840,031 A | 11/1998 | Crowley | |
| 5,843,103 A | 12/1998 | Wulfman | 606/159 |
| 5,849,023 A | 12/1998 | Mericle | |
| 5,879,361 A | 3/1999 | Nash | 606/159 |
| 5,897,567 A | 4/1999 | Ressemann et al. | 606/159 |
| 5,916,227 A | 6/1999 | Keith et al. | 606/159 |
| 5,938,670 A | 8/1999 | Keith et al. | 606/159 |
| 5,938,672 A | 8/1999 | Nash | 606/159 |
| 5,957,941 A | 9/1999 | Ream | 606/159 |
| 5,976,165 A | 11/1999 | Ball et al. | 606/180 |
| 6,015,420 A | 1/2000 | Wulfman et al. | 606/168 |
| 6,080,170 A | 6/2000 | Nash et al. | 606/159 |
| RE36,764 E * | 7/2000 | Zacca et al. | 606/159 |
| 6,096,054 A * | 8/2000 | Wyzgala et al. | 606/170 |
| 6,146,395 A | 11/2000 | Kanz et al. | 606/159 |
| 6,156,048 A | 12/2000 | Wulfman et al. | 606/159 |
| 6,183,487 B1 | 2/2001 | Barry et al. | 606/159 |
| 6,217,549 B1 | 4/2001 | Selmon et al. | 604/106 |
| 6,416,526 B1 * | 7/2002 | Wyzgala et al. | 606/170 |
| 6,451,037 B1 * | 9/2002 | Chandrasekaran et al. | 606/159 |
| 6,503,261 B1 * | 1/2003 | Bruneau et al. | 606/159 |
| 6,565,588 B1 * | 5/2003 | Clement et al. | 606/180 |
| 2002/0010487 A1 * | 1/2002 | Evans et al. | 606/180 |

* cited by examiner

INTRALUMENAL MATERIAL REMOVAL SYSTEMS AND METHODS

CROSS-REFERENCE TO RELATED APPLICATIONS.

This application claims priority under 35 U.S.C. §119(e) from U.S. Provisional Patent Application Nos. 60/194,805, filed Apr. 5, 2000; 60/194,952, filed Apr. 5, 2000 and 60/194,998, filed Apr. 5, 2000 and is a continuation-in-part of U.S. patent application Ser. No. 09/724,914, filed Nov. 28, 2000. The disclosures of these applications are incorporated herein by reference in their entireties.

BACKGROUND OF INVENTION

The present invention relates to systems and methods for removing material, such as obstructions and partial obstructions, from any body lumen of a mammalian subject, such as a blood vessel, a portion of the gastrointestinal tract, a portion of the dural spaces associated with the spinal cord, or the like. More particularly, the present invention relates to systems, system components, and methods for removing material from a lumen of a mammalian subject using an advanceable, rotating cutter assembly.

DESCRIPTION OF PRIOR ART

Removal of atherosclerotic obstructions and partial obstructions using rotating cutter assemblies is a well-established therapeutic intervention. Numerous atherectomy methods and devices have been conceived and developed. Most of these systems involve placement of a guide wire, a guiding catheter and a cutting device in proximity to an obstruction or partial obstruction in a blood vessel and then advancing and rotating the cutting device to cut or ablate the obstruction.

The following U.S. patents describe many types and specific features of atherectomy devices: U.S. Pat. Nos. 4,898,575; 5,127,902; 5,409,454; 5,976,165; 5,938,670; 5,843,103; 5,792,157; 5,667,490; 5,419,774; 5,417,713; 4,646,736; 4,990,134; 4,445,509; 5,681,336; 5,695,507; 5,827,229; 5,938,645; 5,957,941; 5,019,088; 4,887,613; 4,895,166; 5,314,407; 5,584,843; 4,966,604; 5,026,384; 5,019,089; 5,062,648; 5,101,682; 5,112,345; 5,192,291; 5,224,945; 4,732,154; 4,819,634; 4,883,458; 4,886,490; 4,894,051; 4,979,939; 5,002,553; 5,007,896; 5,024,651; 5,041,082; 5,135,531; 5,192,268; 5,306,244; 5,443,443; 5,334,211; 5,217,474; 6,183,487; 5,766,190, 5,957,941 and 6,146,395. These U.S. patents are incorporated by reference herein in their entireties.

Despite the many and varied approaches to atherectomy systems and methods exemplified by the U.S. patents cited above, many challenges remain in providing systems and methods for removing material from a lumen, such as a blood vessel, safely and reliably and without causing complications. The safety and reliability of the system is manifestly critical. Recovery of the debris generated during an atherectomy operation, or maceration of the debris to a particle size that will not produce additional blood vessel clogging or damage, is essential. The flexibility and size of the system is also an important feature. Control features and the ease of use of the system by a surgeon or other medical professional are additional important features.

One of the particular challenges of removing material from the interior of lumens is that the drive and cutter assemblies must be small enough and flexible enough to travel, over a guidewire, to a desired material removal site, such as the site of an obstruction or occlusion. Yet, the drive and cutter assemblies must be large enough and have structural integrity sufficient to operate reliably and effectively to cut or ablate the obstruction. Additionally, removal of the debris from the material removal site using an aspiration system is generally desirable. The drive and cutter assemblies therefore desirably incorporate a debris removal system as well.

The size and consistency of the material comprising the obstruction are frequently not well characterized prior to introduction of the material removal device. Thus, although devices and cutters having different sizes and properties may be provided, and may even be interchangeable on a materials removal system, it is difficult to ascertain which combination of features is desired in any particular operation prior to insertion of the device. The use of multiple cutter assemblies having different properties during a materials removal operation is inconvenient at best, since it requires removal of each independent device and interchange of the cutter assemblies, followed by reinsertion of the new cutter assembly, or of a new device entirely. Interchange and reinsertion of cutter assemblies is time consuming and generally deleterious to the health and condition of the patient undergoing the procedure.

Many different types of expandable cutters have been conceived in an effort to provide a cutter having a small diameter profile that may be delivered to and removed from the site of the desired material removal, and that is expandable at the site to provide a larger diameter cutter. The following U.S. patents disclose various approaches to expandable cutter assemblies: U.S. Pat. Nos. 5,540,707; 5,192,291; 5,224,945; 5,766,192; 5,158,564; 4,895,560; 5,308,354; 5,030,201; 5,217,474; 5,100,425; and 4,966,604. These patents are incorporated by reference herein in their entireties.

Although many approaches to expandable cutter assemblies have been developed, none of these approaches has, to date, been known to be implemented in a commercially successful atherectomy system.

SUMMARY OF INVENTION

One aspect of the present invention involves the therapeutic application of methods and systems for translumenal microsurgery using advanceable, rotating cutter assemblies to conditions and disorders in addition to atherectomy and cardiology applications. Methods and systems for translumenal microsurgery using advanceable, rotating cutter assemblies of the present invention may be implemented, for example, in treatment of blood vessel conditions and for removal of accumulations of materials in blood vessels in applications other than cardiology and in blood vessels remote from the heart; in treatment of benign prostate hyperplasia; in the treatment of gynecological conditions involving accumulation of material in fallopian tubes and elsewhere, such as fibrotic disease; in treatment of urological conditions, such as kidney stones; in treatment of gallbladder conditions, such as gall stones; and in the treatment of spinal cord and dural tube conditions, such as stenoses of the spinal canal.

Methods and systems of the present invention involve placement of a material removal component, referred to herein as a "cutter" or "cutter assembly" within a lumen of a mammalian subject using conventional techniques, such as guidewires and guiding catheters. The intralumenal material removal system includes a cutter assembly positionable in the lumen of a mammalian subject and operably connected to system controls, mechanical and power systems by means of a rotating drive shaft and generally, a stationary guide catheter. The cutter assembly preferably comprises a distal cutting or abrading head having one or more cutting and/or abrading surfaces that is advanceable by translating the drive shaft and rotatable by rotating the drive shaft. The cutter assembly may comprise two or more cutters having different properties.

According to a preferred embodiment of the present invention, the cutter assembly comprises a cutter that is adjustable between a smaller diameter condition, in which it may be guided to and withdrawn from the desired material removal site, and a larger diameter condition, in which it may be operated during a material removal operation. The cutter may thus be introduced to and withdrawn from the material removal site in a retracted, smaller diameter condition that facilitates translation and navigation of the device through various lumens, such as blood vessels. The expandable cutter may be selectively expanded at the material removal site to facilitate cutting, removal and aspiration of the material desired to be removed.

The material removal system preferably provides removal of debris, generally via aspiration through one or more material removal ports in the cutter assembly or another component in proximity to the cutter assembly. Debris generated during a material removal operation is removed by aspiration through the material removal ports and withdrawn through a sealed lumen formed, for example, between the cutter assembly drive shaft and a catheter. The sealed lumen is connectable to a vacuum source and aspirate collection system.

According to another preferred embodiment, the materials removal device of the present invention comprises dual cutting and/or abrading members, one of which is expandable and one of which has a fixed diameter. In one embodiment, a fixed diameter cutter is mounted distal to an expandable diameter cutter. The fixed diameter cutter may take any of a variety of configurations and, according to one embodiment, has a generally ovoid configuration and a plurality of cutting flutes. The fixed diameter cutter may also be provided with ports and/or cutouts that may be selectively employed as aspiration or infusion ports. The expandable diameter cutter, positioned proximal to the fixed diameter cutter, may also be provided with ports that may be selectively employed as aspiration or infusion ports.

In one embodiment, the cutter assembly drive shaft operates bidirectionally and the adjustable diameter cutter is expanded or retracted selectively and controllably upon rotation in opposite directions. Upon rotation of the drive shaft and dual cutter assembly in a first direction, the fixed diameter cutter is used as the primary cutting head and the expandable cutter remains in a smaller diameter condition, while upon rotation of the dual cutter assembly in a second direction, opposite the first, the expandable cutter is in a larger diameter condition and serves as the primary cutter. The present invention uses hydrodynamic, centrifugal and/or frictional forces to expand and contract the dual cutter assembly, thereby obviating the need for additional actuation systems, which add considerable complexity and rigidity to such systems.

Liquid infusion may be provided in proximity to the cutter assembly in addition to or alternatively to aspiration. Infusion of liquids may be used to provide additional liquids for materials removal or to deliver lubricating fluids, treatment agents, contrast agents, and the like. Infusion of fluids in proximity to the area of a material removal operation may be desirable because it tends to reduce the viscosity of the materials being removed, thus facilitating removal through relatively small diameter lumens. Infusion of liquids also desirably tends to reduce the volume of blood removed during the operation. According to one embodiment, a sealed lumen formed between the cutter assembly drive shaft and a catheter may alternatively and selectively be used as an aspirate removal system and an infusion system. The sealed lumen may thus be selectively connectable to a vacuum source and aspirate collection system for aspiration, and an infusion source for infusion of liquids. Ports in or in proximity to the cutter assembly may be thus be employed, selectively, as aspiration and infusion ports.

According to another embodiment, an infusion system may be provided in addition to and independent of the aspiration system. In one embodiment, an infusion sleeve is provided that extends distal to the material removal element. The infusion sleeve is sealed for the length of the catheter and incorporates distal infusion ports. The infusion sleeve preferably extends through the lumen formed by the drive shaft and may be fixed, or preferably, translatable with respect to the dual cutter assembly.

Yet another aspect of the present invention involves the implementation of certain automated and selectable control features. Thus, according to one embodiment, a material removal system of the present invention implements control features based on an operator's input of specified parameters. Specified parameters may include, for example: lesion length, lesion type and character, such as calcified, fibrotic, lipid/fatty, and the like; and/or historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, an automated cutter assembly control unit may calculate and implement automated operating conditions, such as: cutter assembly rotation rate and profile; cutter assembly advance rate and profile; aspiration rate and profile; infusion rate and profile; cutter assembly size and type; and the like.

Another aspect of systems and methods of the present invention involves temperature sensing and control during a material removal operation. Localized temperature increases to temperatures above ambient body temperature can produce an inflammatory response at localized sites, such as at the site of a material removal operation. Localized inflammatory responses can cause a lumen, such as an artery, to narrow or to close completely. Additionally, certain types of plaques and lesions ("vulnerable plaques") are more prone and more sensitive to increased temperatures during a material removal operation using an advanceable and rotatable cutter assembly. Temperature increases during a material removal operation at such vulnerable plaques may produce emboli and may contribute to heart attacks. Restonosis may also occur in a blood vessel following a material removal operation as a consequence of elevated temperatures during the material removal operation.

According to another embodiment of material removal systems and methods of the present invention, a temperature sensor is mounted in proximity to the site of material removal, preferably at the site where the cutter assembly engages the material to be removed, such as a lesion. The temperature sensor is preferably operably connected with a control unit and/or a display device to provide temperature monitoring during a material removal operation. Temperature monitoring at the site of material removal may be integrated with control features in an active or passive manner. In a passive control embodiment, a temperature monitoring feature is provided, enabling the operator performing a material removal procedure to monitor the temperature at the material removal site and manipulate (e.g., adjust advancement and/or rotation of) the cutter assembly appropriately to minimize increases in temperature at the site of material removal. In an active control embodiment, data relating to the temperature, or temperature increases, at the material removal site is provided, intermittently or continuously, to a control system. The control system analyzes the temperature data and minimizes changes in temperature at the site of material removal by automatically changing the advancement and/or rotation profile of the cutter assembly based on the temperature profile. Additional features may be integrated in the control system including, for example, aspiration and infusion flow and flow rates, which may be used to reduce the temperature at the material removal site.

DETAILED DESCRIPTION OF PREFERRED EMBODIMENTS

Figure 1:
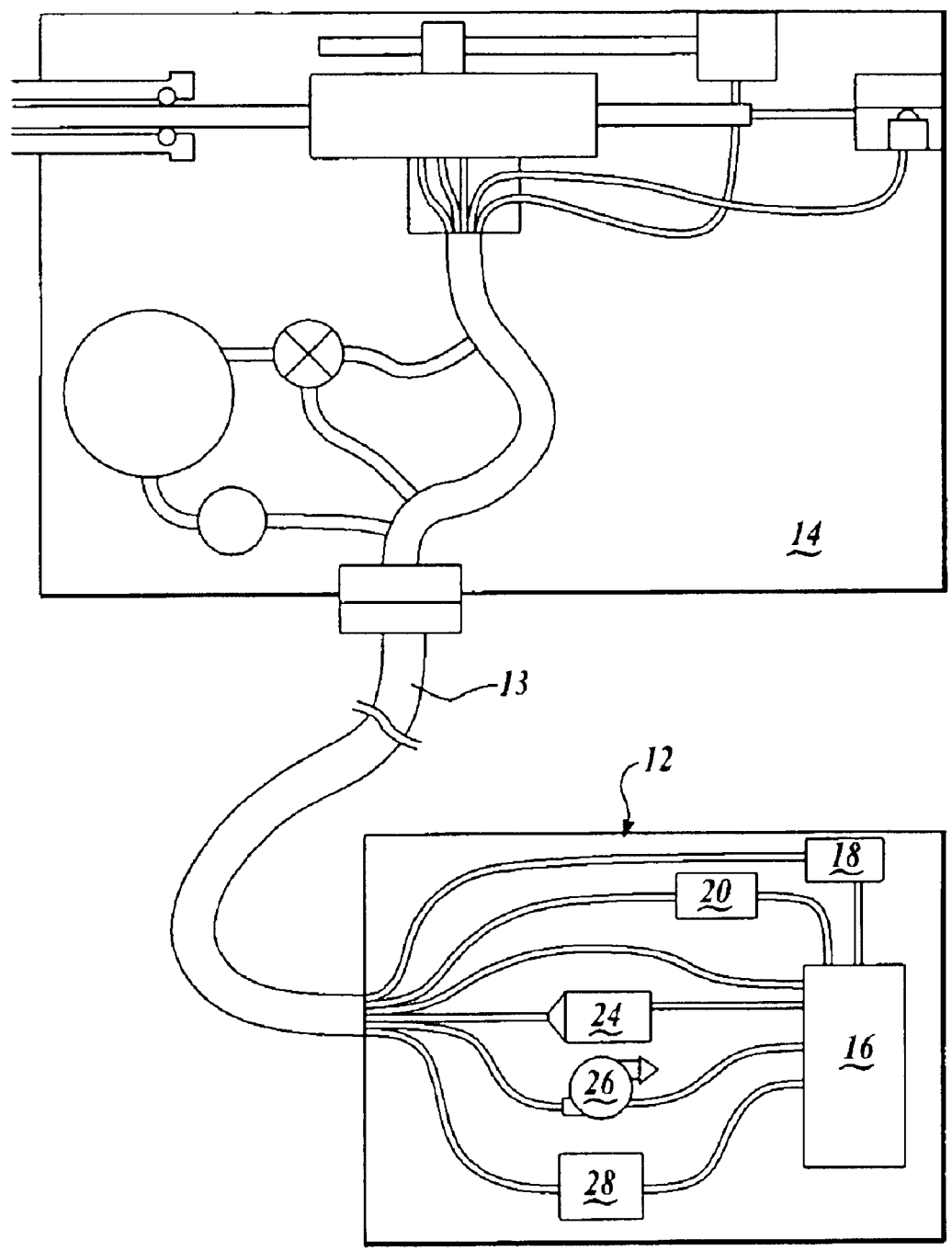
FIG. 1 illustrates a schematic diagram of an exemplary material removal advancer and control system of the present invention illustrating several of the subsystems.

As used herein in the description of various components, "proximal" or "antegrade" refers to a direction toward the system controls and the operator, and "distal" or "retrograde" refers to the direction away from the system controls and the operator and toward a terminal end of the cutter assembly. Wherever appropriate, the same reference numbers have been employed to illustrate and describe the same or similar elements. In general, the dimensions, materials, method of operation and the like used to describe the previous embodiment apply equally to all embodiments presented herein unless stated otherwise. Moreover, various components described herein may be used, combined and interchanged in various combinations. Any of the components described herein may be used with, or substituted for, any of the alternative components that are specifically described. Thus, for example, any of the fixed diameter cutter assemblies may be used in combination with a variable diameter cutter in a dual cutter assembly of the present invention.

In general, the material removal system of the present invention comprises a control unit attached to one end of a catheter assembly and an axially translatable, rotatable drive shaft, a manifold assembly, a catheter assembly, and a cutter assembly positioned at the distal end of the drive shaft. Exemplary material removal systems, components and sub-assemblies are disclosed and described in the U.S. patents incorporated herein by reference.

The cutter assembly is translated over a guidewire to the material removal site, and is actuated at the material removal site to cut, grind or ablate, or otherwise remove, the occlusive material. The control unit, and manifold assembly remain outside the body during a material removal operation. An advancer system may be integrated in the control unit. The advancer may incorporate slip seals for the drive shaft, aspiration and/or infusion connections, and may additionally incorporate a track system for axially displacing the rotating drive shaft and cutter assembly relative to the control unit. The control unit preferably comprises a base arranged so that the control unit may be stably supported on a work surface or a body surface during material removal operations. The control unit also preferably incorporates control systems for actuating, adjusting and providing system information concerning power, drive shaft rpm, drive shaft axial translation, aspiration, infusion and the like.

The material removal system of the present invention incorporates, or is used in conjunction with, a flexible guidewire that is navigated through one or more lumens in a subject, such as blood vessels, to a desired material removal site. Many suitable guidewires are known in the art and may be used with the material removal system of the present invention. Guidewires having a diameter of from about 0.005 inch to about 0.015 inch and having an atraumatic tip are preferred. The catheter assembly generally houses the cutter assembly drive shaft, incorporating a bearing system for rotating the drive shaft and, in some embodiments, defines a lumen for the aspiration and/or infusion of fluids. The catheter assembly may be fixed to and advanced in concert with the cutter assembly drive shaft, or it may be rotatable and/or translatable independently of the cutter assembly drive shaft. The catheter assembly and the guidewire are introduced into a lumen of a patient, such as the femoral artery, and navigated or guided to the site of the desired material removal operation.

A guidewire brake or clamp is preferably provided in proximity to or integrated with the material removal system to hold the guidewire in a stationary, fixed position during operation of the cutter assembly. Rotation and axial displacement of the guidewire may be prevented using either an automatic or a manual grip. An automatic guidewire braking system may be implemented using a solenoid-activated brake that is automatically actuated to brake during activation of the cutter assembly motor drive. A manual guidewire braking system may be actuated by a manual, over-center clamp, cam and brake shoe assembly, or by another mechanical device. An interlock system may be incorporated in connection with a manual brake system to prevent actuation of the cutter assembly drive system if the guidewire is not in a clamped, stationary condition.

An aspiration source and collection vessel may be provided as a commercially available evacuated container having a suitable volume. Alternatively, the aspiration source and collection vessel may be provided as a syringe or similar device actuated by a motor, pressurized gas, or the like. The aspiration source may alternatively be provided as a small, electrical vacuum pump with a suitable collection device.

The configuration and construction of the control unit and the manifold assembly may be of various designs, depending on specific desired applications for intralumenal material removal. Suitable designs and configurations are well known in the art. A control unit is generally provided as a separate unit in electrical and operating communication via a flexible cable with an advancer unit. The advancer unit is configured ergonomically and constructed for placement in proximity to and/or in contact with the patient. The base of advancer unit may be configured, for example, to rest stably on the leg of a patient while a material removal operation takes place. The advancer unit may additionally have a work platform providing a level surface for use of the operator and associated medical professionals.

In the embodiment illustrated in FIG. 1, control unit 12 houses a programmable logic controller and power source 16 in operable communication to provide power and to control operation of vacuum control unit 18, cutter assembly advancer unit 20, guidewire brake unit 22, cutter assembly drive system 24, aspiration control unit 26 and temperature control unit 28. As illustrated schematically, control unit 12 may be provided as a separate console and may incorporate various displays for providing information concerning operating conditions and feedback from the material removal site to the operator. According to one embodiment, control unit 12 provides continuously updated output to an operator including such operating parameters such as temperature at the material removal site; cutter assembly rotation rate and/or advance rate; aspiration rate and/or volume; infusion rate and/or volume; and the like. Control unit 12 may additionally provide adjustable controls permitting the operator to control operating parameters of the cutter assembly and material removal operation. Alternatively, adjustable controls and feedback data may be incorporated in advancer unit 14, or a single integrated control and advancer unit may be provided.

Vacuum control unit 18 may comprise, for example, a solenoid operated vacuum valve. Cutter assembly advancer unit 20 may comprise, for example, a stepper motor. Guidewire brake unit 22 may comprise, for example, a solenoid actuated braking device. Cutter assembly drive system 24 for rotating the cutter assembly may be operated using a pneumatic- or electric-powered motor. Aspiration control 26 may comprise, for example, a vacuum assist motor/pump. Temperature control monitor 28 may be in operable communication with a temperature probe providing continuous or intermittent feedback relating to the temperature or temperature changes at the site of the material removal operation.

In preferred embodiments of the present invention, a high-speed electric motor supplied by a battery power source is utilized for cutter assembly drive system 24. The motor may be geared and/or separated by a short flexible drive shaft that couples the motor to the cutter assembly drive shaft. The motor may thus be mounted off-axis with respect to the drive shaft. This arrangement also permits translation and advancing of the drive shaft independent of the motor, permitting the motor to remain stationary during material removal operations. In alternative embodiments, the motor assembly and other components, such as the drive shaft and cutting assembly may be axially translatable in the advancer unit, as described in more detail below.

According to preferred embodiments of the material removal system of the present invention, the drive system may be unidirectional and capable of rotating drive shaft 25 in one rotational direction, or it may be selectively bi-directional and capable of rotating drive shaft 25 selectively in both a clockwise and counterclockwise direction. Drive system 24 is also preferably capable of rotating drive shaft 25 at variable speeds ranging from 500 rpm to 200,000 rpm, more preferably from 500 to 150,000 rpm. In an exemplary embodiment of the invention, drive system 24 is a direct current variable speed micro-motor capable of operating at rotational speeds of from 500 rpm to 150,000 rpm. It is understood that a variety of motors may be employed in the system and the range of speeds and capabilities may vary according to the type and site of material removed, and the type of cutter assembly utilized. The present invention also contemplates the use of alternative means of rotating drive shaft 25, such as air-driven turbines, and the like.

A proximal end of drive shaft 25 is operably connected directly, or via a coupler or transmission system, to drive system 24, while a distal end of drive shaft 25 is operably connected, directly or via a coupler, to a cutter assembly. Drive shaft 25 is preferably a flexible, hollow, helical, torque-transmitting shaft. Hollow, multi-filar metallic drive shafts are known in the art and are suitable for use with the material removal system of the present invention. Multi-filar stainless steel coil drive shafts having a bi- tri- or quad-filar construction are preferred. Coil drive shafts having an inner diameter of from about 0.015 to 0.025 inch and an outer diameter of from about 0.025 to 0.035 inch are preferred for atherectomy applications.

Figure 2:
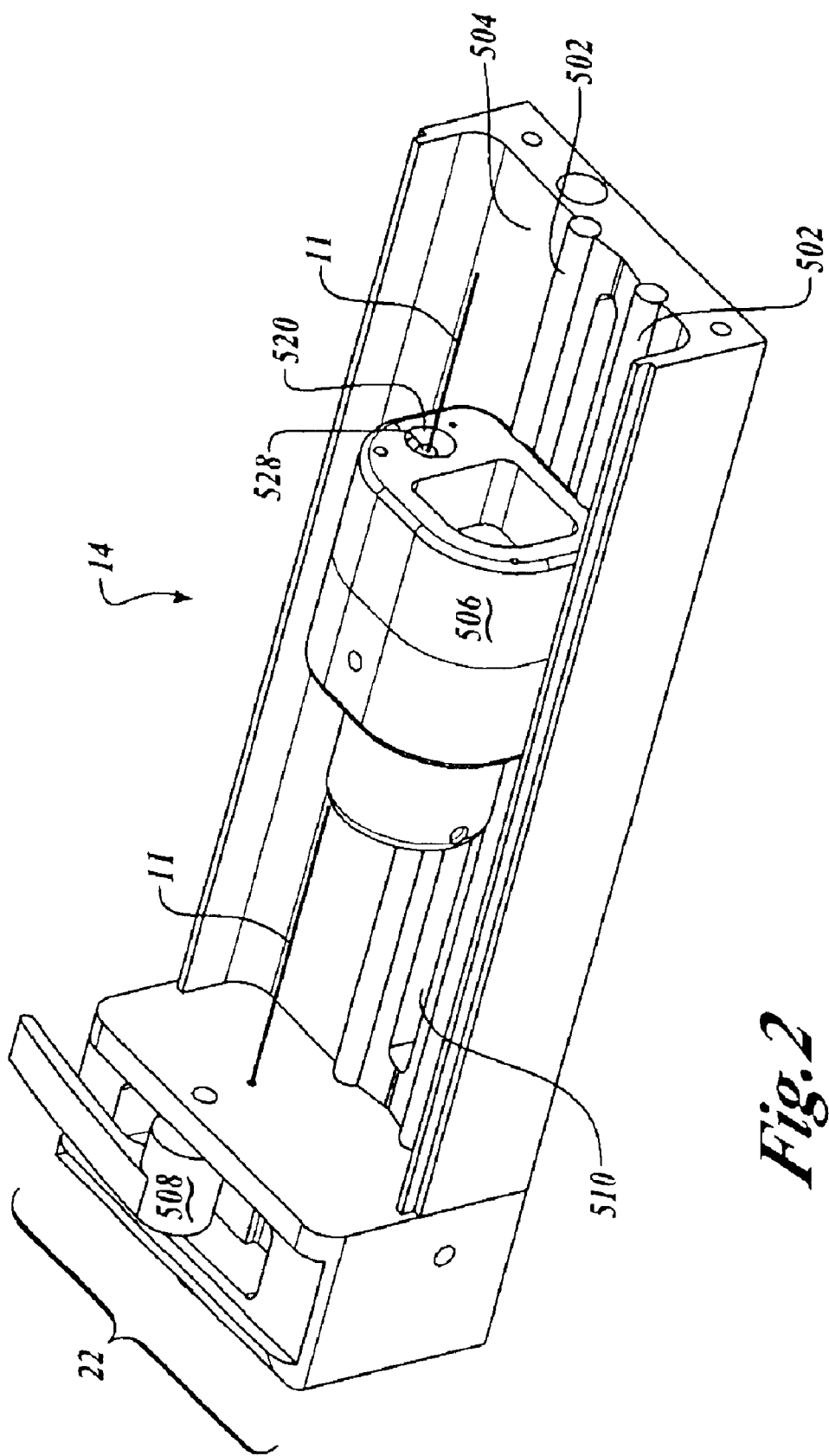
FIG. 2 illustrates a perspective view of an exemplary material removal tracking unit.

FIG. 2 illustrates a preferred embodiment of an advancer 14 for axially translating drive shaft 25 and associated components. Advancer 14 is also referred to herein as a "tracking unit." Tracking unit 14 comprises a structure having one or more axial translation mechanisms, such as rails 502 running along the longitudinal axis of bed 504 on which rides a motor assembly 506. Alternative embodiments of the present invention may employ any conventional axial translation mechanisms including rails, slots, tracks, wheels, and the like. Motor assembly 506 engages rails to permit controllable axial translation in either an antegrade or retrograde direction, which in turn facilitates axial translation of a distal cutter assembly and associated components. Motor assembly 506 may house several components and assemblies, such as, but not limited to one or motors, drive shafts, gear drives and the like. In preferred embodiments, one or more drainage apertures and/or reservoirs 510 are provided to facilitate removal of aspirate and other fluids and materials.

A guide wire brake system 22 is fixedly connected to the proximal end of tracking unit 14 to releasably restrict axial and/or rotational movement guide wire 11. In this particular embodiment, a movement-restricting mechanism 508, such as a cam-lever and brake shoe(s) assembly, is housed within guide wire brake system 22. Embodiments of the present invention may incorporate any conventional movement-restriction mechanism or mechanisms that controllably limit axial and rotational movement of guide wire 11. Tracking unit 14 preferably includes a cover protecting motor assembly 506 and bed 504. In addition, a locking mechanism may be provided that controllably restricts axial movement of motor assembly 506. Any conventional locking mechanism may be employed in the present invention, such as, but not limited to a system whereby a restrictive force is exerted from tracking unit cover to motor assembly 506. For example, an element may extend from the top face of motor assembly through a longitudinal slot in the tracking unit cover, and may be held in tight association with the cover by a clamping device, such as a threaded knob.

Figure 3:
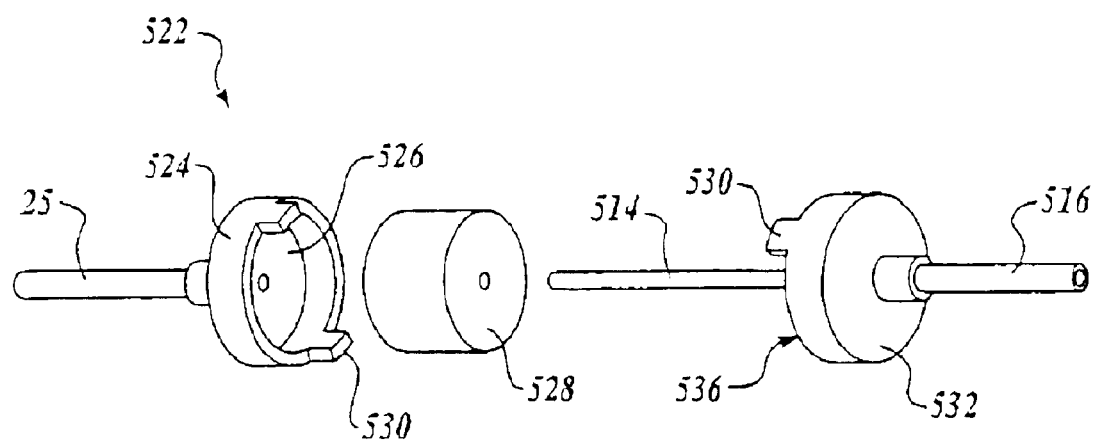
FIG. 3 illustrates an enlarged, exploded view of an exemplary magnetic coupler assembly.
Figure 4:
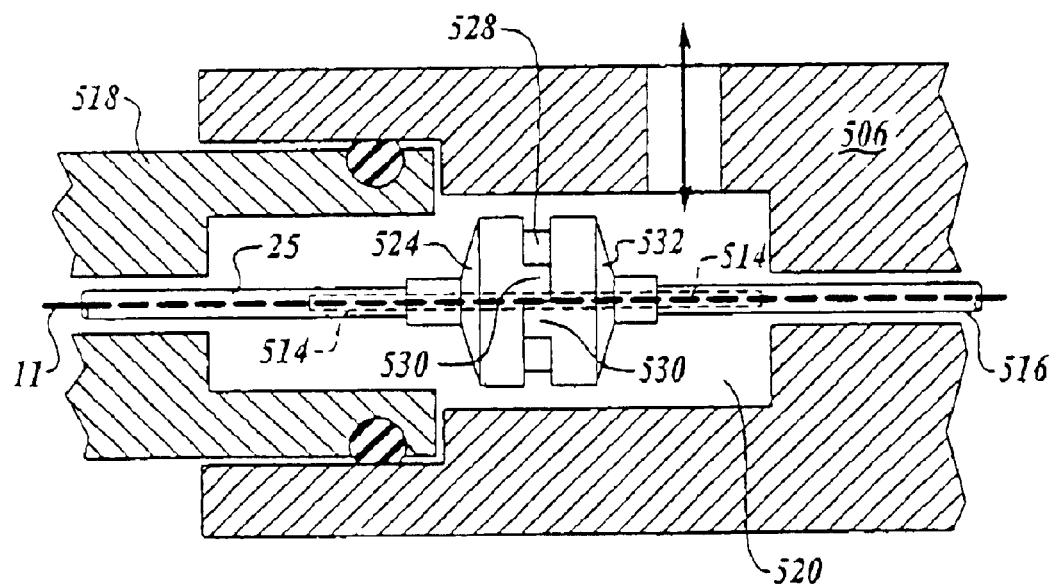
FIG. 4 illustrates an enlarged, partially cross sectional view of a magnetic coupling system in association with a drive train, drive shaft and motor housing.

Guide wire 11 passes through brake system 22 into motor assembly 506 and exits from a coupler recess 520 formed in distal face of motor assembly 506. Housed within coupler recess 520 is a drive shaft to drive train coupling assembly. In preferred embodiments, a magnetic coupler assembly 522 is provided, as shown in FIGS. 3 and 4. In one embodiment, magnetic coupler 522 comprises a drive shaft connector 524 having a first magnet recess 526 for receiving and magnetically engaging one or more magnets 528, as well as a plurality of anti-slip cogs 530. A complementary drive train connector 532, also having a plurality of anti-slip cogs 530, has one or more magnets 528 fixedly connected to drive train connector recess 536. Drive train connector 532 further comprises a guide tube 514, which passes through complementary central apertures of drive train connector 532 and magnet 528 to extend beyond the distal face of magnet 528. Guide tube 514 serves to align and guide drive shaft connector 530 to properly seat and releasably engage magnet 528 of drive train connector 532. Drive shaft connector 524 is provided with a central aperture for receiving guide tube 514, thereby aligning drive shaft connector 524 with drive train connector 532 and maintaining a concentric arrangement.

FIG. 4 illustrates magnetic coupler assembly 522 in the context of coupler recess 520 of motor assembly housing 506. In this illustration, drive shaft connector 524 has releasably engaged drive train connector 532 by passing guide tube 514 through central aperture of drive shaft connector 524 and magnetically adhering to magnet 528 such that anti-slip cogs 530 are offset and engaged. In operation, rotational movement is imparted to drive train 516 by any conventional drive system, whereby rotational movement is transferred to drive shaft connector 524 by engaging complementary anti-slip cogs 530 on each connector. Drive shaft 25 is fixedly connected to drive shaft connector 524 by any conventional methods, such as welding, laser welding, soldering, brazing, adhesive bonds and the like. Rotational movement imparted to magnetic coupler assembly 522 by drive train 516 is effectively transferred to drive shaft 25 and the distal cutter assembly. Magnetic coupler 522 is designed to accommodate guide wire 11. Drive train 516 and all distal components are provided with a central aperture to receive guide wire 11, thereby permitting free axial translation of guide wire through the entire system.

Figure 5:
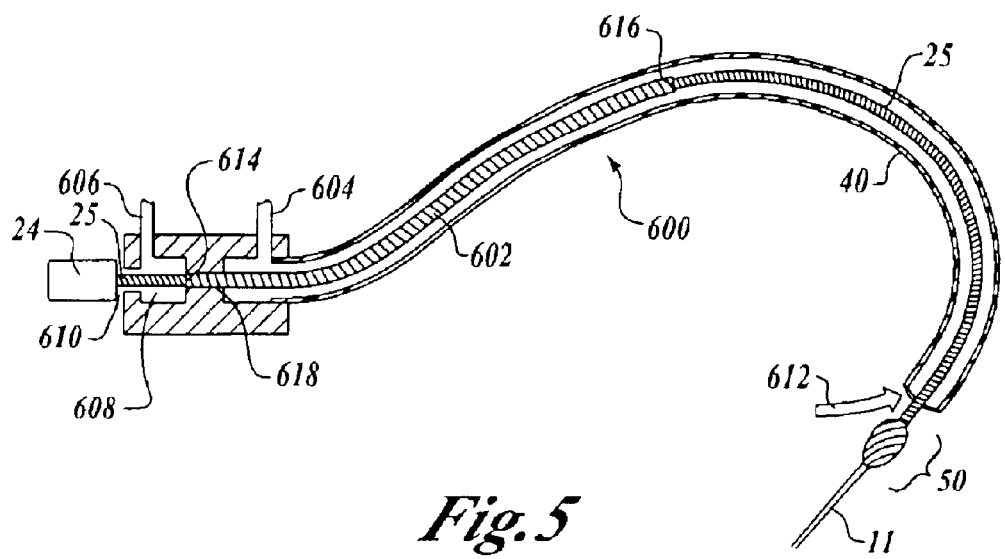
FIG. 5 illustrates an enlarged, partially cross sectional view of an exemplary embodiment of a flexible low-friction fluid seal assembly around a rotating drive shaft.

FIG. 5 illustrates an exemplary embodiment of a flexible, low-friction fluid seal assembly 600 which permits free rotation and axial translation of a drive shaft while effectively separating a zone of substantially atmospheric pressure and a zone of low-pressure. A thin, flexible tube, referred to herein as a fluid seal tube 602, having a wall thickness of from about 0.0001–0.010 inch, preferably from about 0.0005–0.005 inch, and more preferably from about 0.001–0.0015 inch, encases drive shaft 25 with a clearance between the inner wall of fluid seal tube 602 and drive shaft 25 of from about 0.0001–0.025 inch, preferably from about 0.0005–0.01 inch, and more preferably less than 0.002–0.004 inch. Fluid seal tube 602 may comprise any suitable material that may be formed as a thin tube that is very flexible, tough and possesses high thermal resistance, such as conventional polymer-based tubing, preferably polyimide tubing coated with polytetrafluoroethylene (PTFE) and the like. Suitable tubing is commercially available, for example, from Microlumen Corporation, Tampa Fla.

Proximal end of drive shaft 25 passes through fluid seal tube 602 and is operably connected or coupled to drive system 24. Proximal end 614 of fluid seal tube 602 is held in tight association with fluid seal tube seat 618 formed in the manifold of advancer unit 14, such as by any conventional mechanical and/or chemical bonding, sealing, adhering, clamping, retaining technologies, so as to form an air and water-tight seal with the fluid seal tube seat of the manifold unit. Proximal end 614 of fluid seal tube 602 extends proximally and may be adjacent an infusion reservoir 608, which is in fluid communication with one or more infusion ports 606 that supply fluid to infusion reservoir 608. Fluid that enters proximal end 614 of fluid seal tube 602 from infusion reservoir 608 is drawn into fluid seal tube by capillary action and other forces. Excess fluid within infusion reservoir 608 may pass through one or more overflow apertures 610. Overflow apertures 610 may have a diameter, for example, of from about 0.005–0.25 inch, preferably from about 0.01–0.10 inch, and more preferably from about 0.02–0.04 inch in diameter. Distal end 616 of fluid seal tube 602 is open and extends an operable distance along the axial length of drive shaft 25, such that fluid surface tension and head loss prevent fluid from moving the fall distal length of fluid seal tube, even under high vacuum conditions. For example, fluid seal tube may be about 2–25 inches in length, depending on the particular embodiment, preferably about 4–18 inches in length and more preferably about 5–12 inches in length.

In operation, vacuum is applied to one or more aspiration ports 604, creating a zone of low pressure within a flexible catheter arrangement, and inducing fluid flow in direction of arrow 612. This arrangement creates an effective seal around a high-speed driveshaft as it enters into an area of high vacuum, while effectively preventing loss of vacuum at proximal end 614 of fluid seal tube, which operates under substantially atmospheric pressure, thereby permitting near frictionless rotation of drive shaft 25. Preferred embodiments may include additional features, such as one or more aspiration/infusion portal(s), through which aspirate may be removed from and infusion materials may be introduced into various catheter systems.

Additionally, systems of the present invention may employ a plurality of connecting devices of any conventional design and type to facilitate connecting various catheters and sheaths to various components. A wide variety of "quick-connect" devices are well known in the art and may be used throughout the system of the present invention. Such connecting devices may provide a fluid-tight seal. For example, FIG. 4 depicts a connector 518 forming a fluid-tight seal with coupler recess 520 of motor assembly housing 506, which may be further connected to one or more catheters and/or sheaths of the present invention. This design, and modifications that are well known in the art, enable the operator to quickly and efficiently change and exchange components of the present invention.

A conduit for aspirate may be integrated into the hollow, helical, torque-transmitting drive shaft by bonding or shrinking a polymer onto the outer and/or inner surface(s) of the coil drive shaft. DuPont's TEFLON® brand polytetrafluoroethylene (PFTE) is an especially preferred polymer for sealing the drive shaft. For many applications of the material removal system of the present invention, utilization of a non-compressible multi-filar metallic coil drive shaft without an integrated aspirate conduit is preferred, with one or more conduit(s) for aspiration and/or infusion being provided internally or externally coaxial with the drive shaft, or as a bi-axial conduit. Assemblies of this type may be constructed from materials that provide enhanced system flexibility and guidance properties.

In one preferred embodiment of the present invention, the flexible, hollow, torque-transmitting drive shaft comprises a self-dampening drive shaft having a "multi-helical" configuration, herein referred to as a multi-helical drive shaft, or simply as a drive shaft. In practice, helically wound drive shafts tend to experience expansion" upon sudden rotational movement at high rpm. Depending upon the "lay" of the helical structure and the direction of rotation, helical drive shafts undergo transitory expansion or contraction caused by unwinding or cinching of the helical structure in response to the applied torque, resulting in axial displacement of the cutting device. This undesirable axial displacement of the drive shaft can pose a potential problem for rotational debulking devices and one potential problem is uneven loading and unloading of a distal bearing retaining a cutter. A multi-helical drive shaft has adjoining sections of "left-lay" and "right-lay" helical configurations, each section of substantially equivalent length. The "left-lay" and "right-lay" sections may be arranged along the length and longitudinal axis of the multi-helical drive shaft in any operable configuration. For example, half the drive shaft length may comprise one continuous length of one lay, and the remaining, substantially equal length, of the drive shaft may comprise one continuous length of opposite lay. Alternatively, a plurality of alternating sections of opposite lay sections of any length may be provided such that, in sum, the multi-helical drive shaft has a substantially half left-lay and a substantially half right-lay configuration.

A multi-helical drive shaft having adjoining lengths of oppositely wound helical coils dampens the movement of adjoining, counterpart section(s). For example, upon counterclockwise rotation, left-lay coiled section(s) of the drive tend to unwind, causing axial displacement in the distal direction, while the right-lay section(s) of the drive shaft will tend to contract, causing axial displacement in the proximal direction. The combined opposing forces and actions effectively cancel the axial movement of each respective section, resulting in negligible axial movement of the distal expandable cutter. The multi-helical drive shaft may have any number of opposite-lay sections, provided that opposite-lay sections are properly matched to effectively dampen the axial movement. The opposite lay coils may be joined together directly, or by means of a fixed connection to a conventional coupler interposed between the coils. Such fixed connections may be provided, for example, by welding, soldering, brazing, adhesives and the like.

The catheter assembly provides a sheath that houses the drive shaft and is inserted in a patient, over a guidewire, and guided to a material removal site. The catheter is constructed from a material that is flexible, biocompatible, and impermeable to fluids. The catheter assembly may comprise a plurality of coaxially arranged sheaths and catheters housing rotatable drive shaft 25 and guidewire 11. In a simplified embodiment, a flexible catheter is sealed at a proximal end to control unit 12 and extends to a distal end, in proximity to the cutter assembly. Intermediate catheter systems, manifolds, and the like, may be interposed at various locations along the length of the catheter. The catheter, and/or one or more internal sheath(s), is preferably sealed to provide one or more sealed lumen(s) for aspiration and/or infusion of fluids.

The dimensions and preferred materials of construction for catheters are well known in the art. The desired dimensions of the catheter(s) depend upon the material removal application and site, and the configuration and placement of aspiration and/or infusion conduits. The outer diameter of the catheter is smaller than the inner diameter of all anatomical lumens through which it is intended to be guided, and the inner diameter of the catheter is large enough to accommodate internal components, as described in greater detail below. A proximal end of the catheter is mounted through a manifold fluid seal located at a distal end of the manifold. The manifold fluid seal may be of any conventional design and provides a fluid-tight seal between the lumen of the manifold, the exterior environment, and the catheter. A distal end of the catheter is preferably in proximity to and/or sealed to a proximal portion of a cutter assembly. According to one embodiment, the catheter is sealed at a proximal end to the manifold and at a distal end to the cutter assembly. In this embodiment, a sealed lumen is provided between the inner surface of catheter and the drive shaft that may be employed as a conduit for aspiration and/or infusion of liquids.

According to another embodiment, a hollow primary sheath is arranged, generally coaxially, within the lumen of the catheter. The outer diameter of the primary sheath is smaller than the inner diameter of the catheter, forming a lumen between the outer wall of the primary sheath and the inner wall of the catheter. A suitable primary sheath may be constructed from any suitable, flexible, biocompatible material. A proximal end of the primary sheath extends into the lumen of the manifold, and a distal end of the primary sheath is operably connected to the cutter assembly, or a fixture in communication with the cutter assembly. Various embodiments of the present invention may employ any number of coaxially arranged catheters and/or sheaths to provide one or more conduits for working components, such as a drive shaft, aspirate and infusion materials, as well as serve as intralumenal delivery vehicles for the expandable cutting assembly.

Figure 6A:
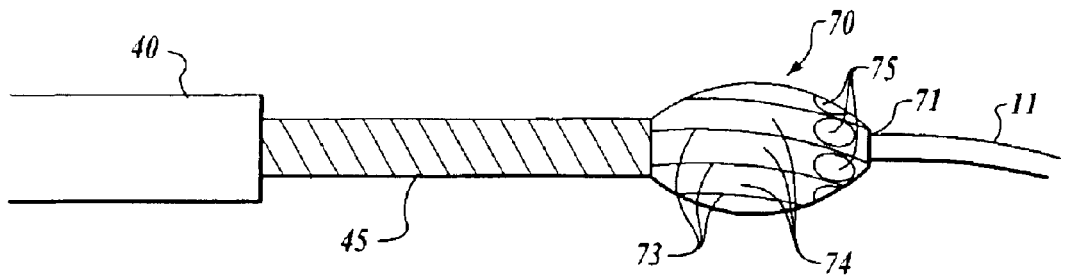
FIG. 6A shows an enlarged schematic perspective view of one embodiment of a cutter assembly of the present invention having ports and being translatable over a guidewire.

FIG. 6A illustrates one embodiment of a cutter assembly of the present invention comprising a generally ovoid cutter head having a plurality of cutting flutes and a plurality of ports providing for aspiration and/or infusion. In the schematic diagrams shown in FIGS. 6A and 6B, ovoid cutter 70 has a central bore 71 that is slightly larger than the outer diameter of guidewire 11 so that cutter 70 is slidable and easily translatable over guidewire 11. In general, central bore 71 is not substantially larger than the outer diameter of guidewire 11. Ovoid cutter 70 has a plurality of cutting flutes 73 having outer cutting surfaces that operate using the principle of differential cutting. Cutting flutes 73 may have sharpened edges to provide cutting and ablation. Cutting flutes 73 may, additionally or alternatively, have an abrasive or cutting material bonded to one or more surfaces. A distal end portion of cutter 70, such as surfaces proximal to the distal opening of bore 71, may additionally or alternatively be provided with abrasive or cutting material. Material such as diamond grit is a suitable abrasive.

At least two cutting flutes 73 are preferably provided. Additional cutting flutes may be provided and arranged in a radially symmetrical configuration. Cutting flutes 73 are separated from one another by depressions 74. One or more depressions 74 is provided with one or more ports 75 providing a passage from the exterior of cutter 70 to an internal cavity 76 of cutter 70. The longitudinal axes of ports 75 are preferably generally aligned parallel to the central axis of ovoid cutter 70 and central bore 71, and ports 75 preferably have a generally uniform diameter. At least two ports 75 are preferably provided. Additional ports 75 may be provided and arranged in a radially symmetrical configuration. In the embodiment illustrated in FIGS. 6A and 6B, a port 75 is provided in each depression 74 formed between adjacent cutting flutes 73. Ports 75 preferably terminate in a distal portion of cutter 70.

Figure 6B:
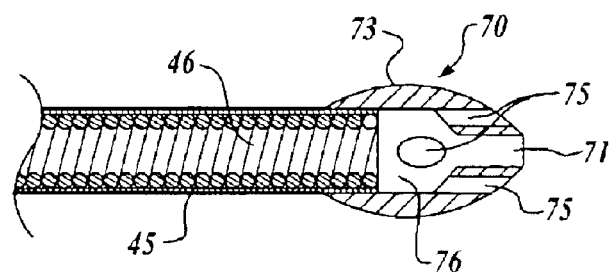
FIG. 6B shows an enlarged schematic cross-sectional view of the material removal device of FIG. 6A along its central longitudinal axis.

As shown in FIG. 6B, the proximal portions of ports 75 preferably terminate in an internal cavity 76 of cutter 70. Internal cavity 76 has a diameter corresponding generally to the outer diameter of the sealed drive shaft, or of a primary sheath or catheter. In the embodiment shown in FIGS. 6A and 6B, a proximal wall of internal cavity 76 of cutter 70 is bonded to a distal outer wall of sealed drive 45, so that cutter 70 rotates with the rotation of sealed drive 45. Sealed drive 45 additionally provides a sealed conduit 46 for passage of fluids and/or particulates being aspirated from a materials removal site through ports 75. Additionally or alternatively, sealed conduit 46 may provide a sealed passage for fluids being delivered to a materials removal site for infusion through ports 75. As shown in FIG. 6A, sealed drive 45 and cutter 70 are positioned distal to catheter 40 during a material removal operation.

Figure 7A:
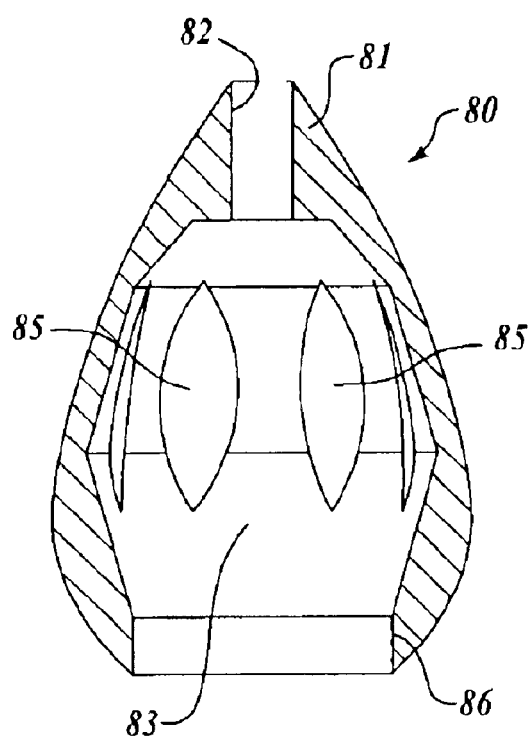
FIG. 7A shows an enlarged schematic cross-sectional view of another embodiment of a cutter of the present invention.
Figure 7B:
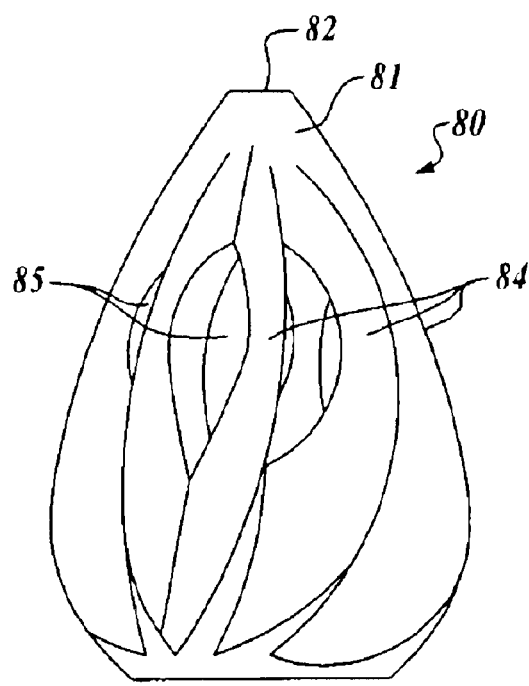
FIG. 7B shows an enlarged schematic plan view of the cutter of FIG. 7A.

FIGS. 7A and 7B illustrate another cutter configuration of the present invention. Cutter 80 comprises a distal guide tip 81 having a central bore 82 through which a guidewire is slidably engageable. Cutter 80 has an internal cylindrical cavity 83 having a diameter greater than that of central bore 82. Cutter 80 also comprises a plurality of cutting flutes 84 arranged in a radially symmetrical configuration. Cutting flutes 84 are preferably provided with sharpened cutting edges. Cutting flutes 84 are generally thin and narrow, separated from one another by ports 85. Ports 85 are provided as relatively large openings to internal cavity 83 and are created by removing a substantial amount of material between adjacent cutting flutes 84. Ports 85 terminate in a proximal portion of cutter 80 to provide a collar 86 that is sealed to sealed drive shaft 45 or a catheter or sheath. Cutter 80 is bonded to sealed drive 45 so that cutter 80 rotates with the rotation of sealed drive 45, and so that sealed drive 45 provides a sealed passage for fluids and/or particulates being aspirated through ports 85. Additionally or alternatively, sealed drive 45 may provide a sealed passage for fluids being infused to a materials removal site through ports 85.

Figure 8A:
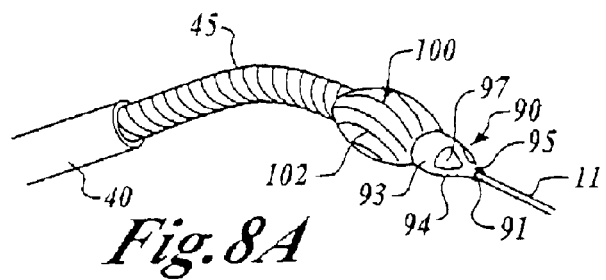
FIG. 8A shows an enlarged schematic perspective view of a cutter assembly of the present invention having dual cutting members and aspiration ports.
Figure 8B:
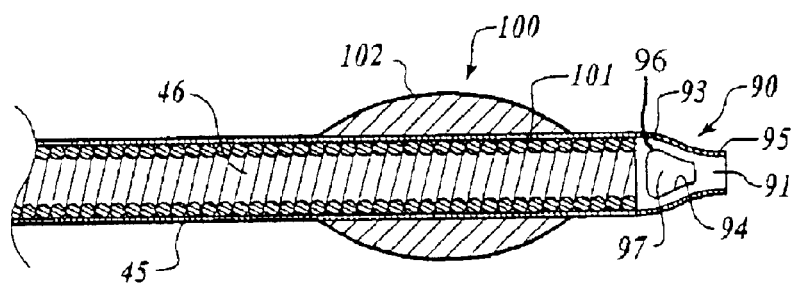
FIG. 8B shows an enlarged schematic cross-sectional view of a cutter assembly similar to the cutter assembly of FIG. 8A having dual cutting members and aspiration ports.

FIGS. 8A and 8B show one embodiment of a composite cutter assembly of the present invention. This cutter is referred to as composite because it has multiple configurations of cutting surfaces. In this embodiment, distal cutter 90 has a central bore 91 sized and configured for translation over guidewire 11. Distal cutter 90 has a hollow cylindrical base 93 and at least two cutting blades 94 joining cylindrical base 93 to a guide tip 95. Cutting blades 94 preferably have one or more sharpened edges to provide cutting and ablation. Cutting blades 94 may, additionally or alternatively, have an abrasive or cutting material bonded to one or more surfaces. Material such as diamond grit, etc. is suitable. At least two cutting blades 94 are preferably provided. Additional cutting blades may be provided and arranged in a radially symmetrical configuration. Guide tip 95 is cylindrical and hollow, is of a diameter less that that of base 93, and incorporates central bore 91 for slidably receiving guidewire 11. This type of cutter is described in detail in U.S. Pat. No. 5,019,088, which is incorporated by reference herein in its entirety. Distal cutters of the type described in detail in U.S. Pat. Nos. 4,887,613 and 4,895,166, which are also incorporated by reference herein in their entireties, may also be used in connection with the present invention.

Distal cutter 90 has an internal cavity 96 accessed by ports 97 defined by adjacent cutting blades 94. Cylindrical base 93 of distal cutter 90 may have an inner diameter that generally matches the outer diameter of sealed drive shaft 45, with a proximal, inner surface of base 93 bonded directly to a distal, exterior surface of sealed drive shaft 45, as illustrated in FIG. 8B. In this embodiment, fluids and debris may be withdrawn through ports 97, and through lumen 46 sealed drive shaft 45 to a collection device during a cutting cycle. Alternatively, fluids may be delivered from an infusion reservoir through lumen 46 of sealed drive shaft 45 and through ports 97 to a material removal site. Alternatively, cylindrical base 93 of distal cutter 90 may be bonded directly to a proximal cutter 100, as illustrated in FIG. 8A.

Proximal cutter 100 has a hollow central bore 101 and comprises one or more cutting or abrading surfaces 102. In the embodiment illustrated in FIG. 8A, a distal end of proximal cutter 100 is sealed to a proximal end of distal cutter 90, and a proximal end of proximal cutter 100 is sealed to a distal end of sealed drive shaft 45. In this embodiment, proximal cutter 100 may be provided with ports providing access to central bore 101 and the lumen of sealed drive shaft 45. In another embodiment, illustrated in FIG. 8B, proximal cutter 100 is sealed to sealed drive shaft 45 along central bore 101 and may be separated a distance from distal cutter 90. In either event, proximal cutter 100 may comprise a plurality of cutting surfaces, such as cutting flutes. Alternatively, exterior portions of proximal cutter 100 may have an abrasive surface, such as a surface having diamond grit applied thereon, for cutting or abrading materials.

Figure 9A:
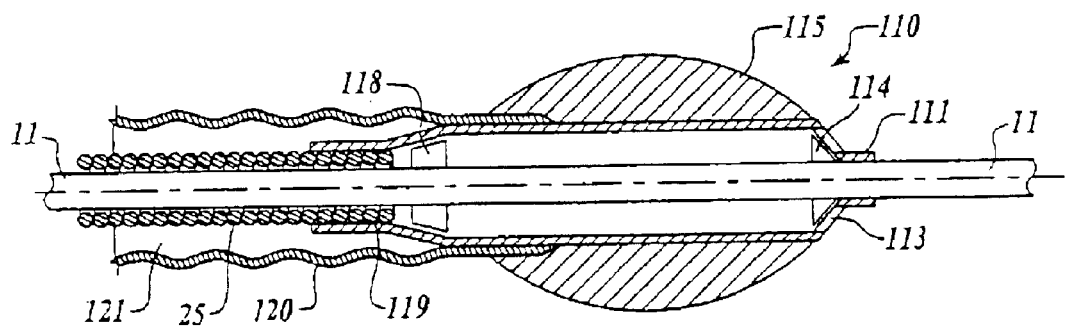
FIG. 9A shows an enlarged schematic cross-sectional side view of a cutter assembly and associated aspirating lumen of the present invention.
Figure 9B:
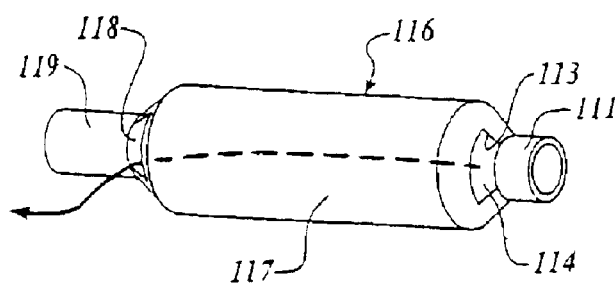
FIG. 9B shows an enlarged schematic perspective view of an aspirating tube and cutter component of the cutter assembly of FIG. 9A.

FIGS. 9A and 9B illustrate another embodiment of a cutter assembly 110 that is an integrated combination of cutters similar to the proximal and distal cutters described with reference to FIGS. 8A and 8B. The distal region of cutter 110 has a guide tip 111 providing translation of the cutter over guidewire 11. Cutting blades 113 extend proximally from guide tip 111 and have a flared or conical configuration. Cutting blades 113 preferably have one or more sharpened edges to provide cutting and ablation as the cutter is advanced over the guidewire into materials desired to be removed. Cutting blades 113 may, additionally or alternatively, have an abrasive or cutting material bonded to one or more surfaces. At least two cutting blades 113 are preferably provided. Additional cutting blades may be provided and arranged in a radially symmetrical configuration. Distal ports 114 providing access to a central conduit are located between cutting blades 113.

Cutting blades 113, or a distal extension or collar joined to the cutting blades, is sealed to or formed integrally with a proximal burr 115 having one or more cutting or abrasive surfaces. According to one embodiment, proximal burr 115 is mounted on an integrated aspirating tube and cutter 116 illustrated in FIG. 9B. In this embodiment, aspirating tube and cutter 116 comprises guide tip 111, cutting blades 113, distal ports 114, a central conduit defined by tube 117, proximal ports 118 and a proximal collar 119 having a diameter smaller than that of tube 118. All of these components are preferably radially symmetrical with respect to a central axis and guidewire 11.

Proximal burr 115 is preferably mounted on an exterior surface of tube 117, as shown in FIG. 9A. Proximal collar 119 is preferably sealed to a distal end of a torque transmitting drive shaft 25, which may be sealed or unsealed. In another preferred embodiment, a distal end of catheter 120 is sealed between an exterior surface of tube 117 and an interior diameter of proximal burr 115. Catheter 120 is thus sealed to cutter assembly 110 and rotates with cutter assembly 110 and drive shaft 25, but it is not torque transmitting. In this embodiment, a lumen 121 is formed between catheter 120 and drive shaft 25 that is in communication with proximal ports 118 and distal ports 114 of cutter assembly 10. Lumen 121 provides a conduit for aspiration of fluids and debris from a materials removal site and, alternatively, a pathway for infusion of fluids to a materials removal site. Catheter 120 is preferably constructed from a material that is flexible enough to provide accurate and convenient translumenal guidance of the cutter and catheter to a material removal site, yet stiff enough to avoid deformation of the catheter during aspiration or placement at the material removal site. According to one embodiment, the wall of catheter 120 has a smooth, corrugated outer surface to facilitate translumenal guidance of the cutter and drive shaft/catheter assembly.

Figure 10A:
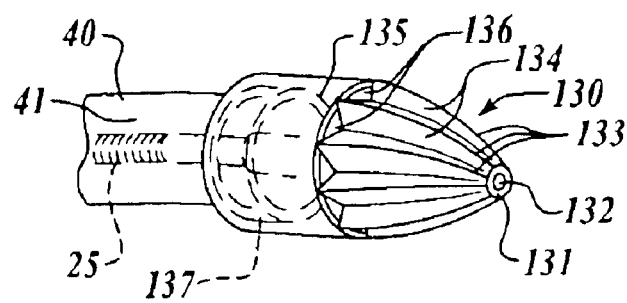
FIG. 10A shows an enlarged schematic side view of another embodiment of a cutter assembly of the present invention.
Figure 10B:
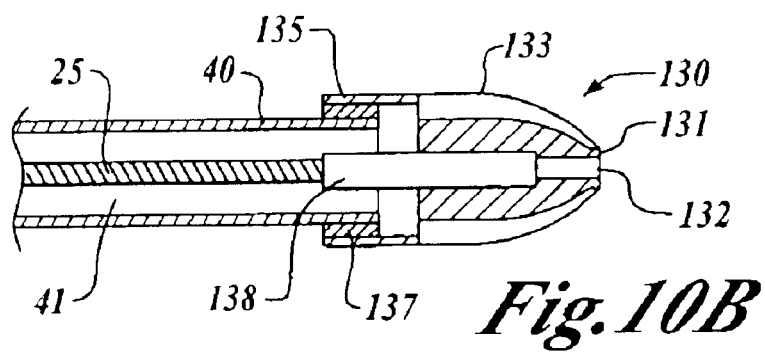
FIG. 10B shows an enlarged schematic cross-sectional view of the cutter assembly of FIG. 10A.
Figure 10C:
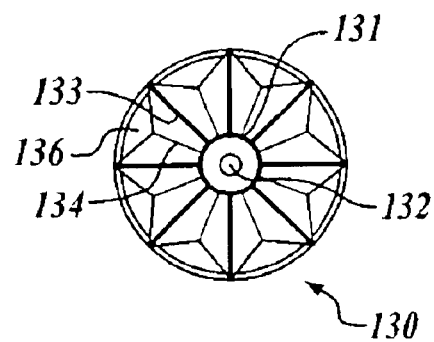
FIG. 10C shows an enlarged schematic end view of the cutter assembly of FIGS. 10A and 10B.

FIGS. 10A–10E illustrate additional embodiments of cutters and cutter assemblies of the present invention. FIGS. 10A, 10B and 10C illustrate a cutter 130 having a guide tip 131 and central bore 132 providing translation of the cutter over a guidewire. Cutter 130 comprises a plurality of cutting flutes 133 extending proximally from guide tip 131. Cutting flutes 133 flare outwardly in a proximal direction; the outer diameter of cutter 130 increases, preferably linearly, in a proximal direction. Cutting flutes 133 are separated from one another by depressions 134 having an increasing depth, compared to the profile of cutting flutes 133, in a proximal direction.

Figure 10D:
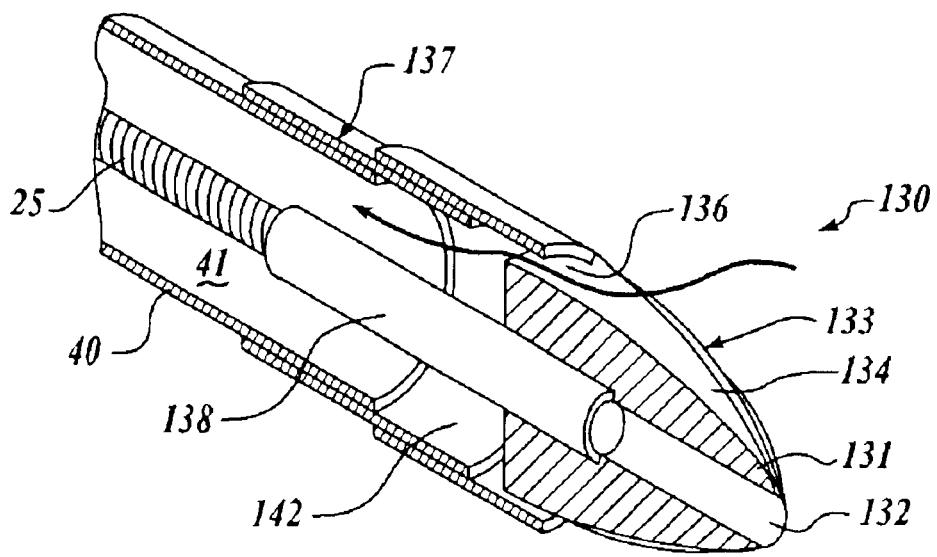
FIG. 10D shows an enlarged, partially cut-away and partially cross-sectional view of the cutter assembly of FIG. 10A.

As shown in FIGS. 10B and 10D, a proximal portion of cutter 130 is mounted on a cylindrical outer coupler 135, producing ports 136 between the inner diameter of coupler 135 and depressions 134 of cutter 130. Ports 136 have a generally triangular or semicircular cross-section, depending on the profile of depressions 134. A distal portion of outer coupler 135, such as a steel tube, and a proximal portion of cutter 130 are mounted to one another in sealed and fixed relationship, such as by laser welding. A proximal portion of outer coupler 135 is rotatably mounted to a bearing 137 providing a fluid-tight, high tolerance seal. Bearing 137 is bonded to a distal portion of catheter 40. A drive coupler 138 is fixedly mounted to a distal portion of drive shaft 25 and to a proximal wall of central bore 132 of cutter 130. These components are preferably mounted to provide a desired space between the proximal end portion of cutter 130 and the distal end portion of bearing 137 and catheter 40.

Drive shaft 25, drive coupler 138, cutter 130 and outer coupler 135 rotate upon rotation of the drive shaft during a material removal operation, while catheter 40 and bearing 137 do not rotate during material removal. A continuous conduit is thus provided from ports 136 to the lumen 41 formed between drive shaft 25 and catheter 40. This lumen and port access to the site of a material removal operation may provide aspiration of fluids and debris from and/or infusion of liquids to the material removal site.

Figure 10E:
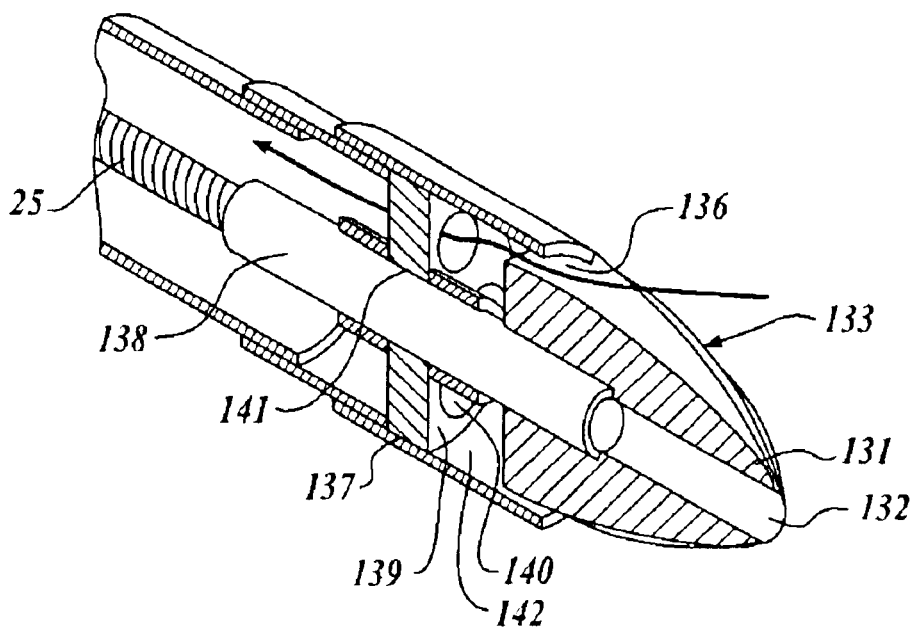
FIG. 10E shows an enlarged, partially cut-away and partially cross-sectional view of a cutter assembly of FIG. 10A additionally comprising a stationary bearing with through ports.

As shown in FIG. 10D, bearing 137 may be a cylindrical bearing having a relatively thin wall and an inner diameter forming a part of the continuous lumen for aspiration or infusion of fluids. Alternatively, as shown in FIG. 10E, bearing 137 may be provided, at a distal region, with a circular member 139 having a plurality of through ports 140 and a central bore 141 having a diameter corresponding generally to the outer diameter of drive coupler 138. The number and size of through ports 140 may vary with particular applications of a material removal system. Through ports 140 are provided in a radially symmetrical arrangement with respect to the axis of rotation, and have a sufficient cross-section to remove desired volumes of fluids and particulates. Circular member 139 of bearing 137 is mounted to drive coupler 138 so that bearing 137 remains stationary as drive coupler 138 and drive shaft 25 rotate using, for example, a thrust bearing. Bearing 137 is thus bonded to an outer surface of catheter 40 and bearing 137, with circular member 139 and ports 140, are stationary as drive shaft 25, drive coupler 138 and cutter 130 rotate during a material removal operation.

The embodiment of FIG. 10E, employing a stationary, ported bearing, is particularly suitable for use in aspirating fluids and debris from the site of material removal. As material is cut by blades 133, it is entrained in fluids and passes through ports 136 to a collection space 142 provided between the proximal end portion of cutter 130 and the distal end portion of bearing 137. As cutter 130 rotates at generally high rotational speeds, shear forces are generated by rotation of the cutter. The combination of vacuum forces used for aspiration and the stationary ported bearing 137 tend to break down and macerate solids in collection space 142, facilitating aspiration of solids entrained in the fluid flow through bearing ports 140.

Figure 11A:
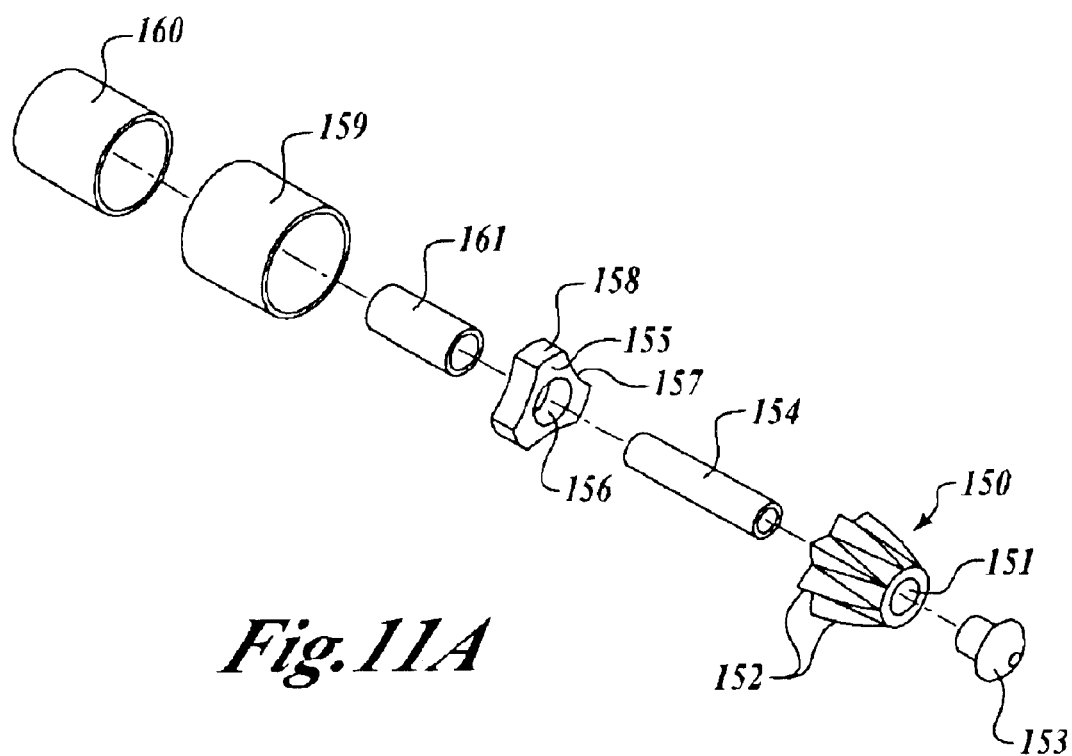
FIG. 11A shows an enlarged perspective, exploded view of a cutter assembly of the present invention incorporating a stationary bearing having through ports.
Figure 11B:
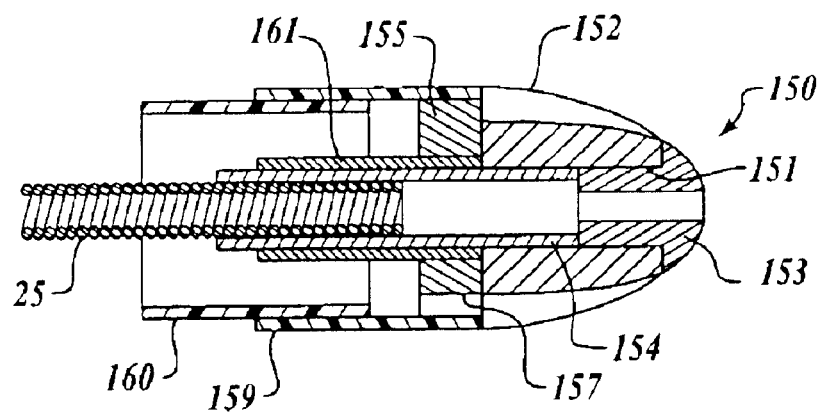
FIG. 11B shows an enlarged, cross-sectional view of the cutter assembly of FIG. 11A, additionally illustrating dimensions suitable for atherectomy applications.

FIGS. 11A and 11B illustrate yet another material removal assembly of the present invention in which a cutter 150 having a central bore 151 and a plurality of cutting blades 152 is provided in combination with a stationary bearing having a non-circular configuration to provide a cutter assembly. This embodiment employs a guide tip 153 having a central bore in slidable relationship to the guidewire and that is mounted on a distal end of cutter 150. This type of separate guide tip may be used with many of the cutter assemblies disclosed herein.

The embodiment of FIGS. 11A and 11B also employs a tubular cutter shaft 154 mounted to central bore 151 of cutter 150 at a distal end and mounted to a drive shaft coupler at a proximal end. A stationary bearing 155 having a central bore 156, cutouts 157 and peripheral surfaces 158 is mounted in a housing 159, for example by welding. Peripheral surfaces 158 have a configuration matching that of the inner wall of housing 159, while spaces between cutouts 157 and the inner wall of housing 159 form a plurality of ports for aspiration and/or infusion of fluids.

Housing 159 is bonded to a spacer 160, and the inner surface of spacer 160 is bonded to an outer surface of a catheter or sheath that provides a conduit for aspiration and/or infusion. Cutter 150 is bonded to cutter shaft 154, which is in turn bonded to a bearing stop 161, which is bonded to a distal end of drive shaft 25. Bearing stop 161 is rotatably engaged within central bore 156 of stationary bearing 155 to provide rotation of cutter 150 with rotation of drive shaft 25, while the catheter or sheath, spacer 160, housing 159 and stationary bearing 155 may remain rotationally stationary during a materials removal operation. While various components of the cutter assembly are rotatable with respect to one another, they are linked to provide axial displacement of the cutter assembly and drive shaft, catheter assembly and any associated sheaths as a unit.

Figure 12:
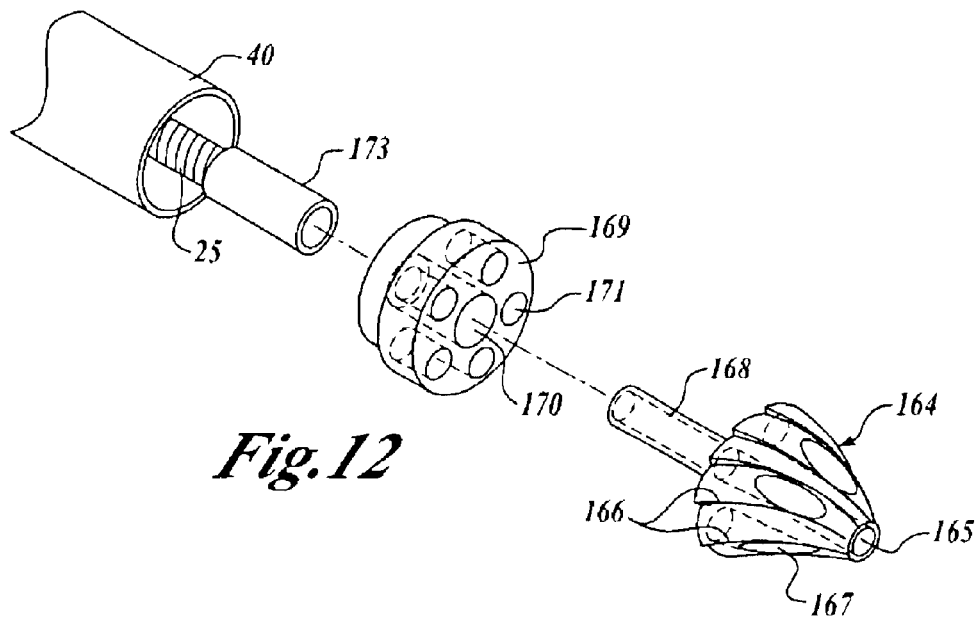
FIG. 12 shows an enlarged, exploded view of yet another embodiment of a cutter assembly of the present invention incorporating a stationary bearing.

FIG. 12 illustrates another embodiment of a material removal system of the present invention having a material removal assembly comprising a rotatable cutter in proximity to a stationary bearing or stator. As shown in FIG. 12, cutter 164 has a central bore 165 for passage of a guidewire, a plurality of cutting flutes 166, a plurality of ports 167, and a hollow mounting shaft 168. Mounting shaft 168 traverses, at least partially, a central bore 170 in stationary bearing or stator 169, and is bonded to a distal portion of drive coupler 173, which is bonded, at a proximal portion, to drive shaft 25. A plurality of through ports 171 is provided in stationary bearing 169. Through ports 171 preferably have longitudinal axes generally parallel to and concentric with the axis of rotation of drive shaft 25. Stationary bearing or stator 169 may have a stepped configuration such that a distal portion in proximity to cutter 164 has a larger diameter than the proximal portion, which is bonded to an inner surface of catheter 40. The diameter of a distal portion of stationary bearing 169 preferably generally matches or is slightly less than the largest diameter of cutter 164 at its proximal end measured at the outer surface of cutting blades 164.

The cutter assembly of FIG. 12 operates similarly to the cutter assembly described with reference to FIG. 10E, in which drive shaft 25, drive coupler 173, mounting shaft 168 and cutter 164 rotate during a material removal operation, while stationary bearing 169 with through ports 171 bonded to catheter 40 remain stationary during a material removal operation. A continuous passage for aspiration or infusion of fluids is provided by cutter ports 167, stationary bearing through ports 171, and a lumen formed between drive shaft 25 and the inner surface of catheter 40.

Figure 13A:
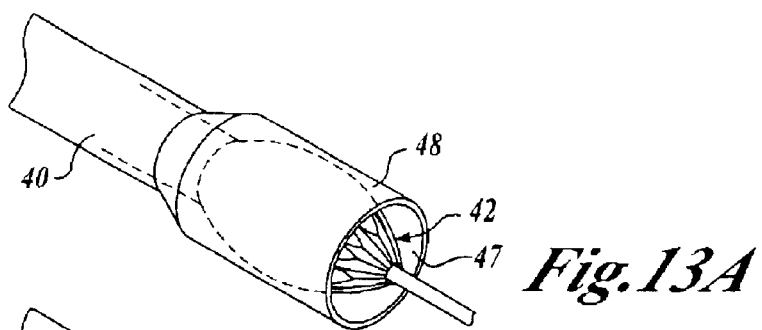
FIG. 13A shows an enlarged, perspective view of another embodiment of a material removal device of the present invention having a cutter assembly in a retracted position inside an enlarged distal catheter section.
Figure 13B:
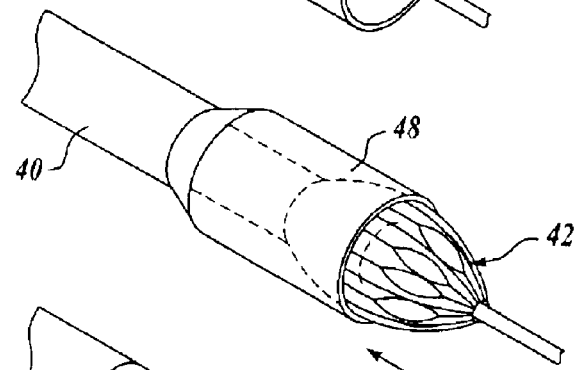
FIG. 13B shows an enlarged, perspective view of the material removal device of FIG. 13A with the cutter assembly in a partially extended position.
Figure 13C:
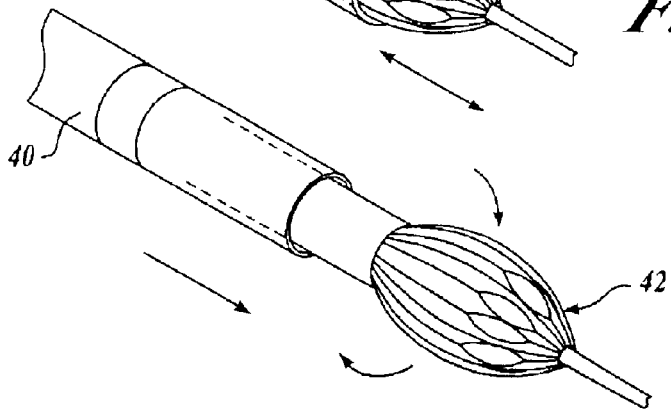
FIG. 13C shows an enlarged perspective view of the material removal device of FIG. 13A with the cutter assembly in an extended position distal to the enlarged distal catheter section.

FIGS. 13A–13C illustrate yet another embodiment of a material removal system of the present invention. An enlarged cutter assembly housing may be provided at a distal end of catheter 40 or a primary sheath. In one embodiment, the cutter assembly housing may be provided as a continuous, enlarged section of catheter 40 or a primary sheath that accommodates a cutter assembly 42. The hollow interior of cutter housing 48 defines an interior space 47 in which the cutter assembly 42 resides when axially retracted in a proximal direction. The interior space 47 of cutter housing 48 may be continuous, for example, with sealed lumen 41 of catheter 40, creating a conduit for the flow of various fluids during aspiration and/or infusion. In another embodiment, the distal end of a primary sheath, or catheter 40, is operably connected to a flared coupling that serves as a cutter assembly housing.

In operation, it may be desirable to alternate between advancing and retracting cutter assembly 42 to facilitate the aspiration of particulates, especially particulates that are too large to pass through ports provided in the cutter assembly. For example, retracting cutter assembly 42 in a retrograde direction within cutter housing 48 or a flared primary sheath during aspiration creates a laminar-like flow, thereby more effectively drawing fluid and particulates into housing 48 and permitting particulates to be further broken down by the grinding action of the rotating cutter assembly within housing 48. Larger particulates may thus be broken down to a size that can be withdrawn, with fluids, through aspiration ports and into the lumen of catheter 40 or a primary sheath for collection.

Figure 14A:
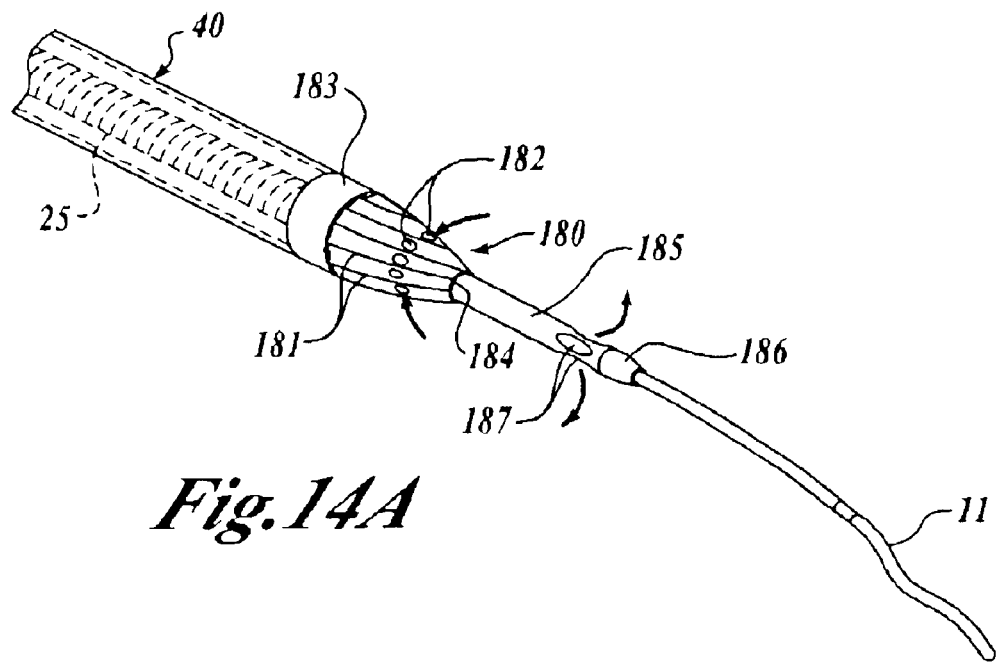
FIG. 14A shows an enlarged, perspective view of yet another embodiment of a material removal device of the present invention having a cutter assembly incorporating a stationary bearing and an infusion lumen and sleeve for infusion of fluids distal to the cutter assembly.
Figure 14B:
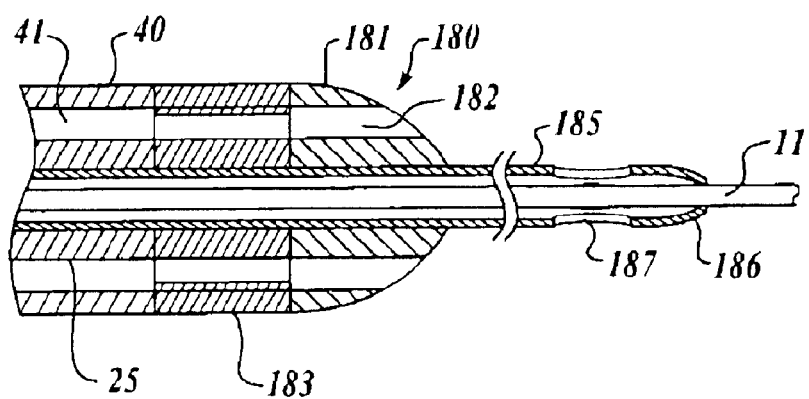
FIG. 14B shows an enlarged cross-sectional view of the material removal device of FIG. 14A illustrating the infusion sleeve and the infusion lumen.

FIGS. 14A and 14B illustrate yet another embodiment of a material removal system of the present invention incorporating an infusion conduit and sleeve for infusion of fluids independent of and in addition to aspiration ports and an aspiration conduit. According to preferred embodiments, an infusion sleeve and infusion ports are positionable distal to a cutter assembly to provide infusion of liquids retrograde to the cutter assembly and aspiration ports. As shown in FIGS. 14A and 14B, cutter assembly 180 comprises a cutter head having a plurality of cutting surfaces 181 and a plurality of aspiration ports 182. Cutter assembly 180 may also comprise a stationary bearing 183 having a plurality of through holes providing passage of particulate debris entrained in fluids from aspiration ports 182 to sealed lumen 41 formed between an inner surface of catheter 40 and an outer surface of drive shaft 25. Cutter assembly 180 is fixedly mounted to drive shaft 25 to provide rotation of cutter assembly 180 with drive shaft 25.

Cutter assembly 180 is additionally provided with an enlarged central guide bore 184 in which infusion sleeve 185 is mounted and, preferably, axially translatable. Infusion sleeve 185 is preferably a hollow sheath having an inner diameter larger than the outer diameter of guidewire 11, having a guide tip 186 for receiving guidewire 11 in an axially translatable fashion, and having a plurality of infusion ports 187. The outer diameter of infusion sleeve 185 is preferably smaller than the inner diameter of drive shaft 25, and infusion sleeve 185 is preferably concentric with and retained within the lumen of drive shaft 25. The inner surface of infusion sleeve 185 preferably forms a sealed lumen within drive shaft 25 and generally concentric with the axis of guidewire 11. Sealed lumen 186 is in communication with a source of infusion liquids in or in proximity to control unit 12 and a liquid infusion mechanism, such as a pump, for providing infusion liquids to through infusion ports 187. According to preferred embodiments, infusion sleeve 185 remains rotationally stationary as cutter assembly 180 is rotated. According to another preferred embodiment, infusion sleeve is axially displaceable independent of cutter assembly 180, providing positioning of infusion ports in a desired location with respect to material desired to be removed and the cutter assembly.

As described in greater detail below, a preferred material removal system of the present invention comprises an expandable cutter assembly. The expandable cutter assembly preferably has a dual cutter configuration employing a distal, fixed diameter cutter and a proximal, adjustable diameter cutter. In preferred methods, the dual cutter assembly is rotated and advanced to remove occlusive material in an initial "pilot pass" in which the distal, fixed diameter cutter is the primary cutter, and the proximal, expandable cutter is in a smaller diameter condition. Following one or more pilot passes, the proximal, adjustable diameter cutter is adjusted to a larger diameter condition and the dual cutter assembly is advanced so that the adjustable diameter cutter, in its expanded condition, cuts an even larger volume of occlusive material. Debris and fluids are preferably removed from the site by aspiration. Following removal of desired materials, the proximal, adjustable diameter cutter is adjusted to a smaller diameter condition and the cutter assembly is withdrawn from the site. This method, using the material removal system of the present invention, obviates the need for the operator to remove and replace, or interchange, cutter assemblies during a material removal operation to provide cutters having different diameters and material removal capabilities.

Figure 15:
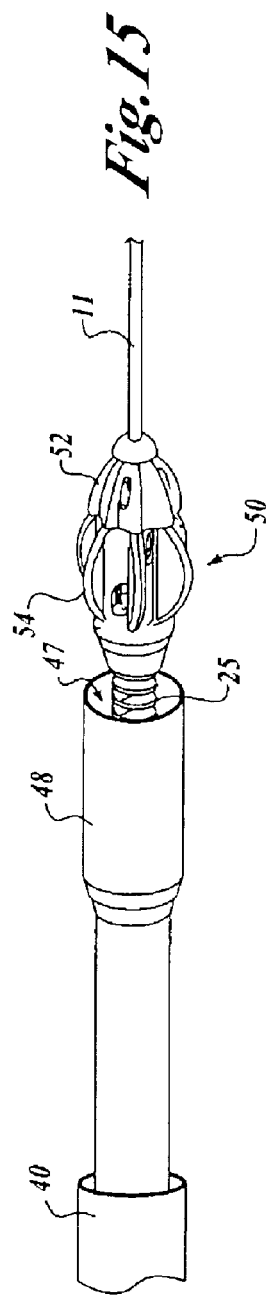
FIG. 15 illustrates an enlarged, perspective view of an exemplary expandable cutter assembly of the present invention in the expanded condition.

FIG. 15 illustrates, schematically, a dual cutter assembly 50 of the present invention, comprising a distal, fixed diameter cutter 52 and a proximal, adjustable diameter cutter assembly 54 adjacent or in proximity to one another. Distal, fixed diameter cutter 52 preferably comprises a plurality of radially symmetrical cutting flutes or blades and a central bore for receiving the guidewire. Any of the previously described cutters may be used, for example, as distal cutter 52. Proximal, adjustable diameter cutter 54 comprises a plurality of flutes, or blades, that are adjustable between a smaller diameter, non-cutting condition and a larger diameter, cutting condition. Adjustment of the cutting blades between the smaller diameter, non-cutting condition and the larger diameter, cutting condition is under operator control. One or both of the cutters may be provided with ports for aspiration and/or infusion.

The dual cutter assembly 50 is generally positioned in proximity to a material removal site when the adjustable cutter is in the smaller diameter, non-cutting condition and adjusted, at the material removal site, to the larger diameter, cutting condition. Adjustment may be accomplished in a variety of ways. According to a preferred embodiment, adjustable diameter cutter 54 is maintained in the smaller diameter, non-cutting condition when it is rotated in a first direction, and is maintained in the larger diameter, cutting condition when it is rotated in a second direction, opposite the first. Thus, distal fixed diameter cutter 52 may serve as the primary cutter when dual cutter assembly 50 is rotated in a first direction, and proximal, adjustable diameter cutter 54 may serve as the primary cutter when dual cutter assembly is rotated in a second direction opposite the first. The dual cutter assembly may thus be delivered to the material removal site in a smaller diameter condition, requiring a smaller diameter delivery system, and adjusted between at least two different diameter cutting positions at the material removal site by adjusting the rotational direction of the drive shaft. Following the material removal operation, the dual cutter assembly is adjusted to the smaller diameter condition and withdrawn from the material removal site.

Figure 16:
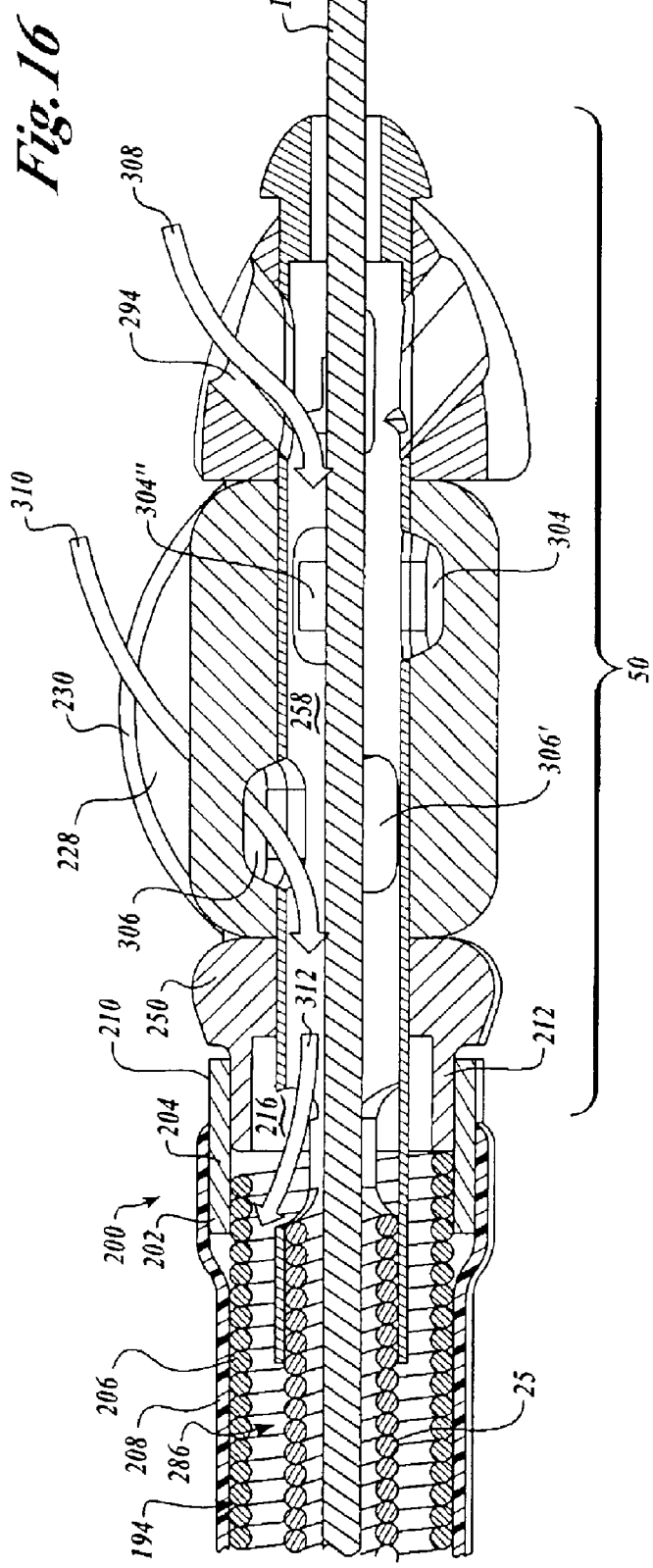
FIG. 16 shows an enlarged, partially cross-sectional perspective view of an expandable cutter assembly of the present invention and associated connections with a drive shaft and flexible conduit catheter.
Figure 17:
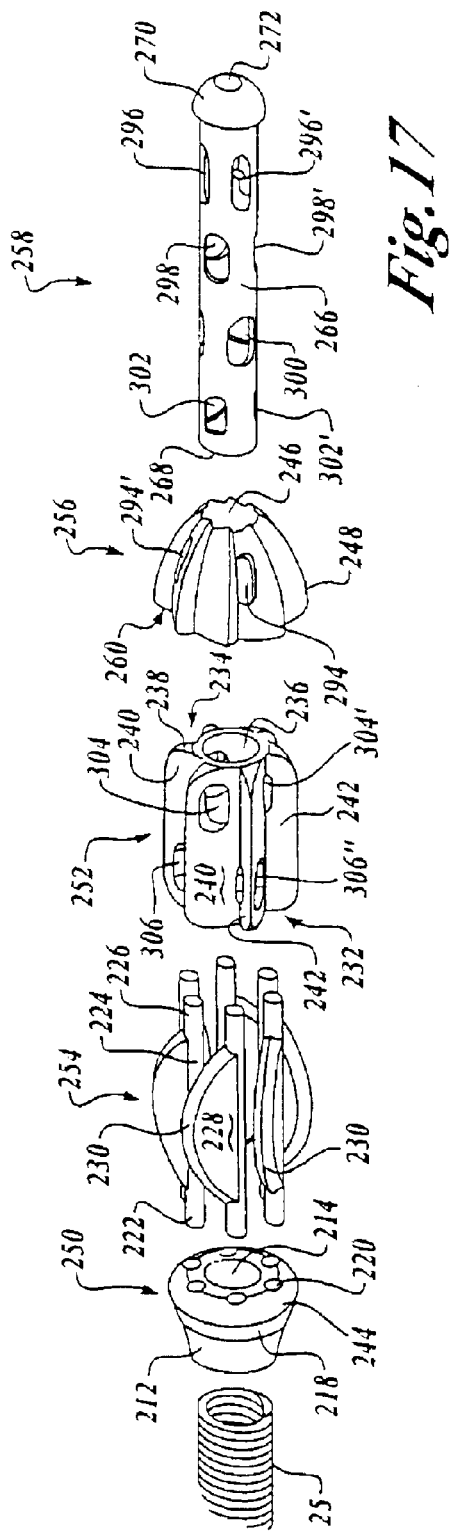
FIG. 17 shows an enlarged, exploded perspective view of an expandable cutter assembly of the present invention.

As illustrated in FIGS. 16 and 17, a distal end of drive shaft 25 is fixedly connected to dual cutter assembly 50. Dual cutter assembly 50, as illustrated in FIGS. 16 and 17, comprises a proximal bushing 250, an adjustable cutter housing a central block 252 and a plurality of pivotable cutting members 254, a fixed diameter distal burr 256 and an assembly tube 258. Preferred materials for the components of dual cutter assembly 50 include metals, metal alloys and ceramics, various types of stainless steels, such as series 300 and/or 400, vanadium steel, nickel-titanium, titanium, titanium-containing metals and oxide ceramics. Variable diameter, expandable cutter assemblies of the present invention and the accompanying drives, catheter assemblies, etc., may be constructed having various sizes and configurations to accommodate different material removal applications and sites. Variable diameter cutter assemblies may be provided in a range of diameters, for example, having a smaller diameter ranging from less than 2 mm to a larger diameter of 5 mm or more. For atherectomy applications, the variable diameter, expandable cutter assembly may have a contracted diameter/expanded diameter of 2.25 mm/2.75 mm, 2 mm/2.75 mm, 1.75 mm/2.5 mm, 1.5 mm/2.0 mm, or the like.

In the embodiment illustrated in FIG. 16, a hollow flexible conduit catheter 194 is coaxially disposed within the lumen of a primary sheath or catheter. Conduit catheter 194 may be constructed from plastic such as polyvinyl chloride (PVC), TEFLON® brand polytetrafluoroethylene (PTFE), Nylon or another polymer, or from a helical metal spring wire encased in a suitable polymer to provide a sealed conduit. Conduit catheter 194 provides a conduit for aspiration and therefore must have sufficient structural integrity to withstand the internal vacuum pressure applied during aspiration, as well as sufficient flexibility to permit guidance and axial movement of the variable diameter, expandable cutter assembly in an atraumatic manner.

In preferred embodiments, conduit catheter 194 is a coiled metallic catheter 206 having a tightly associated flexible outer sheath 208, comprising a material such as TEFLON® that has been "shrink-wrapped" onto the outer surface of the coiled metallic catheter. The present invention comprehends other suitable materials for encasing a coiled catheter, such as any flexible, biocompatible plastic or synthetic material. A sheathing layer may also be applied using techniques other than heat shrinking, such as, for example, plastic extrusion techniques. The outer diameter of conduit catheter 194 is smaller than the inner diameter of catheter 40 or a primary sheath. According to preferred embodiments, conduit catheter 194 has an outer diameter of from about 0.045 to 0.060 inch and an inner diameter of from about 0.035 to 0.050 inch. The lumen formed between conduit catheter 194 and drive shaft 25 serves as a conduit for fluids and particulates during aspiration and perfusion.

A distal end 200 of conduit catheter 194 is fixedly connected to a proximal section 202 of a first slip seal/bearing assembly 204. Slip seal/bearing assembly 204 is a mechanism for coupling conduit catheter 194 to expandable cutter assembly 50, while permitting free rotation of cutter assembly 50 around a central axis and forming a fluid-tight junction between conduit catheter 194 and cutter assembly 50. Outer sheath 208 of conduit catheter 194 extends to partially cover the outer wall of the proximal section of slip seal/bearing assembly 204. A distal section 210 of first slip seal/bearing assembly 204 is in close association with the collar section 212 of proximal bushing 250, thereby forming the slip seal/bearing junction 204. Collar section 212 of proximal bushing 250 is continuous with body section 218 of proximal bushing 250. Proximal bushing 250 has an axially-aligned central aperture 214, which enlarges at collar section 212 to form a proximal bushing conduit 216. The axially-aligned central aperture 214 receives assembly tube 258. Proximal bushing 250 also possesses a first series of receiving apertures 220 radially arranged around central aperture 214 for receiving proximal end 222 of rod section 224 of cutting members 254. The present invention contemplates proximal bushings having various configurations including, for example, a bushing having raised ridges that act as a cutting or grinding burr for removing material when the cutter assembly is operated in a retrograde axial direction.

Figure 18:
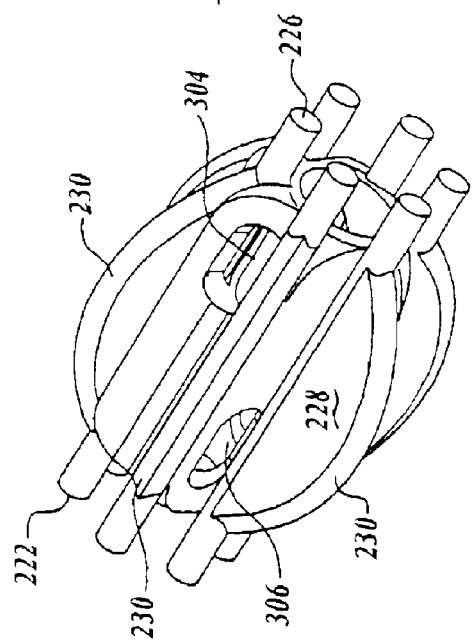
FIG. 18 shows an enlarged, perspective view of cutting members in association with the central block of an expandable cutter assembly of the present invention.
Figure 19A:
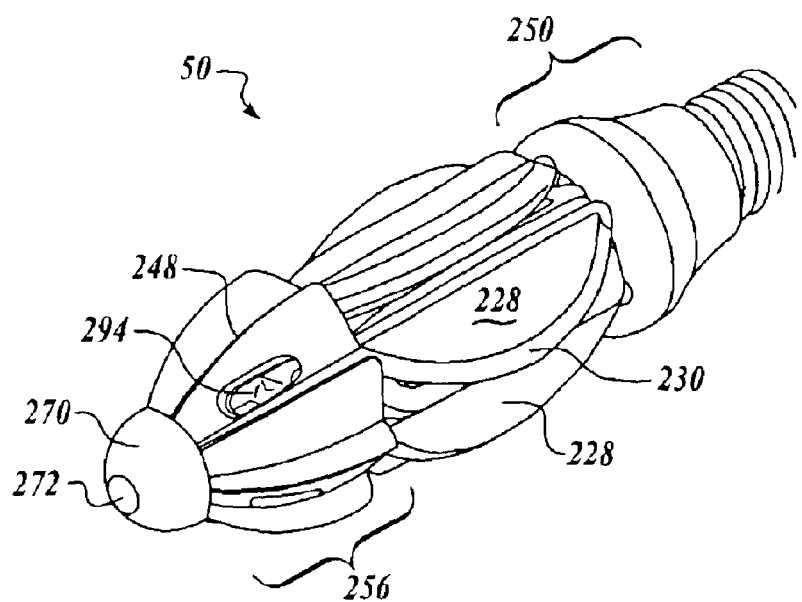
FIG. 19A illustrates an enlarged, perspective view of one embodiment of a dual cutter assembly of the present invention with the cutter assembly in a contracted configuration.
Figure 19B:
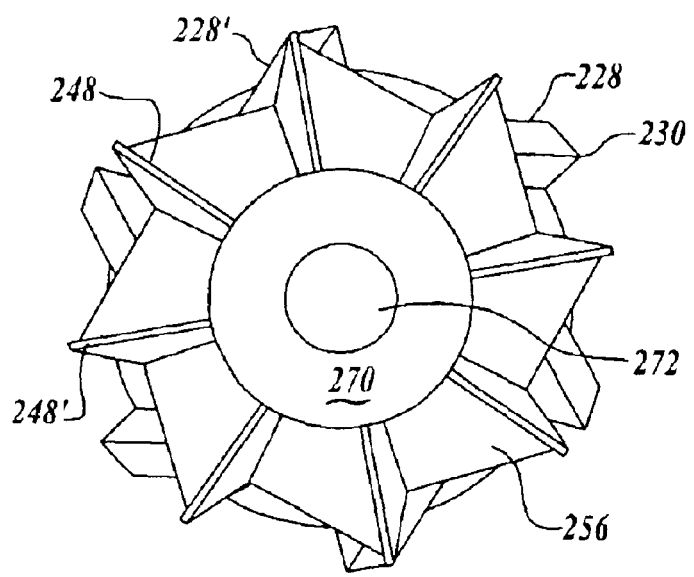
FIG. 19B illustrates an enlarged, front view of one embodiment of the dual cutter assembly of FIG. 19A with the cutter assembly in a contracted configuration.

As shown in FIGS. 17 and 18, cutting members 254 comprise a rod section 224, having a proximal end 222 and a distal end 226. Along the middle portion of each rod section, a blade 228 having a beveled edge 230 for cutting is mounted. It is understood that the beveled edge 230 of the blade(s) may be of different configuration to facilitate the removal of occlusive material. Beveled edges 230 of the blades are preferably designed and configures to operate using the principal of differential cutting, which provides cutting of relatively hard material but does not cut softer tissue, such as the walls of various body lumens. Various angled cutting surfaces may be provided. Rod sections 224 of cutting members 254 are seated onto central block 252.

Central block 252 supports a plurality of cutting members 254 and provides a central lumen 236 for receiving assembly tube 258. Central block 252, having a proximal 232 and a distal end 234, also serves as a control mechanism for the axial rotation of cutting members 254, as explained below. Central block 252 preferably incorporates a plurality of raised spines 238 tangentially arranged around its central axis. Raised spines 238 have a support face 240 and a stop face 242. The junction between raised spines 238 forms a seat for receiving rod sections 224 of cutting members 254. A proximal end 232 of central block 252 may be permanently fixed to a distal face 244 of proximal bushing 250 using any conventional means, such as welds of all types, mechanical attachments and adhesives.

In preferred embodiments, which are illustrated in the accompanying drawings, six cutting members 254 are mounted on a central block configured to support six cutting members. Cutting members 254 are seated in the junctions of raised spines 238 of central block 252, with the blade section 228 of each respective cutting member 254 contacting the support face 240 of the corresponding raised spine 238 of central block 252. The distal end 226 of each rod section 224 of each cutting members 254 extends distally beyond the distal end 234 of central block 252 to engage the proximal face 260 of a distal cutter 256 having a fixed diameter.

As shown in FIGS. 15, 16, 17, 19 and 20, the fixed diameter distal cutter 256 typically has a frusto-conical cross-sectional configuration and a series of raised cutting flutes 248. The raised cutting flutes 248 of distal cutter 256 operate according to the principle of differential cutting to cut, scrape, ablate, grind or otherwise remove occlusive material without damaging other tissues, such as internal blood vessel surfaces. In fact, cutting edges of both distal cutter and cutting members 254, according to the principle of differential cutting, preferentially remove occlusive material while being atraumatic to the more resilient vessel walls. In preferred embodiments, proximal and distal portions of cutting flutes 248 are chamfered to render them atraumatic. It is understood that the distal fixed diameter cutter may be of any suitable configuration, and numerous fixed diameter cutter configurations are known in the art. The dimensions of the distal cutter vary depending upon the particular application and embodiment but, for intravascular applications, the largest outer diameter of the distal, fixed diameter cutter is generally in the range of from about 1.5 mm to 2.5 mm.

Distal cutter 256 is provided with a central aperture 246, which defines a surface for mounting assembly tube 258 and receiving the guidewire. A second series of receiving apertures 264 is present in proximal face 260 of distal cutter 256. Receiving apertures 264 are radially arranged around the central lumen, and complementary to the first series of receiving apertures 220 located on distal face 244 of proximal bushing 250. Receiving apertures 264 receive distal end(s) 226 of rod sections 224 of cutting members 254. In certain embodiments of the present invention, the distal cutter may be fixedly joined by a connection means to the central block. This permanent, fixed connection may be achieved by any conventional means, such as welding, preferably laser-welding, or by soldering, brazing or an adhesive bond between the distal end 234 of central block 252 and proximal face 260 of distal cutter 256.

Assembly tube 258 serves as a connecting means for the expandable cutter assembly 50, as well as a bore for receiving guidewire 11 and a conduit for fluids and debris during aspiration and/or infusion. Assembly tube 258 comprises a body section 266, a proximal end 268 and a distal flanged cap section 270 having a central aperture 272 defining guidance passage 274. A proximal end 268 of assembly tube 258 traverses central aperture 246 of distal cutter 256, and central lumen 236 of central block 252, and central aperture 244 of proximal bushing 250 to fixedly connect with the distal end of drive shaft 25. Distal cutter 256, central block 252 and proximal bushing 250 may be fixedly joined to the assembly tube by any conventional connection, such as welds and adhesives, as well as mechanical connections such as compression fitting. The components of the dual cutter assembly 50 may be drawn in and held in tight association by the distal flanged cap section 270 of assembly tube 258.

The present invention additionally permits the aspiration of fluids and small particulates from a lumen, as well as perfusion of liquids, such as physiologically balanced salt solutions, diagnostic or therapeutic substances, and/or contrast media, into the intralumenal space in proximity to a material removal site. In general, material removal systems of the present invention include a primary aspiration system operating through a primary sheath, and a secondary aspiration system operating through a plurality of ports in cutter assembly 50 and lumen 286 formed between flexible conduit catheter 194 and drive shaft 25, which, in some embodiments, is continuous with lumen of the primary sheath. A proximal end of the primary sheath is operably connected to a vacuum control unit and may incorporate one or more flow-regulation systems, such as valves, seals, manifolds and the like. Upon actuation of the vacuum assembly and opening of the flow-regulation means, a vacuum is created in the lumen formed by primary sheath that draws fluids and particulates from the material removal site and deposits fluids and associated debris in an aspirate collection means.

A secondary aspiration and perfusion system may be provided using a plurality of ports in dual cutter assembly 50 to draw fluids and particulate debris through lumen 274 of assembly tube 258, providing a conduit that is continuous with lumen 286 of flexible conduit catheter 194 and a lumen of a primary sheath. As illustrated in FIGS. 15–20, dual cutter assembly 50 may be provided with a plurality of ports in assembly tube 258, fixed diameter distal cutter 256 and central block 252. Ports 294, 294', etc., in distal cutter 256 communicate with assembly tube ports 296, 296', etc. In preferred embodiments, distal cutter ports 294, 294', etc. are interspaced circumferentially around the distal cutter 256. Central block 252 has a first plurality of circumferentially interspaced ports 304, 304', etc., in the distal portion, and a second plurality of circumferentially interspaced block ports 306, 306' etc., in the proximal portion, which may be arranged in a staggered configuration, as shown. The first plurality of ports 304, 304', etc. define a lumen that is in alignment and continuous with the second group of assembly tube ports 298, 298' etc., and the second plurality of ports 306, 306' etc. define a lumen that is in alignment and continuous with the third group of assembly tube ports 300, 300' etc., such that under vacuum conditions, fluid and particulates flow through cutter ports 294, 294' etc., central block ports 304, 304' and 306, 306' etc. as shown by arrow 308 and 310, respectively. Fluid and particulates continue to flow through assembly tube lumen 274 to a third group of assembly tube ports 302, 302' etc., to lumen 286 of conduit catheter 194, as shown by arrow 312. The infusion of fluids may be provided by switching to an infusion source and reservoir, and reversing flow so that fluid flows through dual cutter assembly 50 in a direction opposite that of directional arrows 308 and 310.

Operationally, the dual cutter material removal system is introduced into the body by way of a lumen, such as a blood vessel, using techniques that are well known in the art. Typically, an access sheath is employed to access the desired vessel at the point of introduction. Through an installed access sheath, the guiding catheter, which houses the guidewire 11, dual cutter assembly 50 and other associated components and serves as a delivery vehicle for those components, is navigated and advanced to the desired site of material removal. In general, the guidewire brake is released and distal end of the catheter is axially translated to a location proximal to the desired material removal site. Guidance and navigation of the catheter and associated cutter assembly may be facilitated by the infusion of fluids, such as contrast media, to monitor the progress of the catheter and/or the cutter assembly. The cutter assembly, or sub-components thereof, may be coated with a radio-opaque material such as gold, platinum, inks and the like, to render the expandable cutting assembly radioscopically visible and to assist a medical professional in guiding and positioning the cutter assembly relative to an occlusion.

Once the guiding catheter is positioned, the flexible conduit catheter, or another internal catheter, is extended distally to facilitate placement of the cutter assembly near the occlusion. The distal end of dual cutter assembly 50 is positioned near a boundary of the occlusion, whereupon the drive system is actuated and drive shaft and dual cutter assembly 50 are rotated. In the embodiment illustrated in the accompanying figures, particularly in FIGS. 19A and 19B, dual cutter assembly 50 is initially rotated in a first (e.g., counter-clockwise) direction, in which the variable diameter cutter is in the smaller diameter condition, and advanced so that distal, fixed diameter cutter 256 cuts and/or abrades and/or ablates the occlusion. In this initial operation and rotation of dual cutter assembly 50, fixed diameter distal cutter 256 contacts the occlusive material and removes occlusive material having a cross-sectional area roughly equivalent to the largest outer diameter of distal cutter 256 and diameter central block 252 and cutting members 254 assembly in their smaller diameter, contracted condition. Initial "pilot passes" may thus remove part of the occlusive material, and subsequent passes may be made by rotating the drive shaft in the opposite direction (e.g., clockwise) to expand the proximal cutter to the expanded, larger diameter configuration to remove additional material. Of course, alternative embodiments of the present invention may be configured to operate in rotational directions opposite to those described above, and different occlusive materials, conditions, locations, and the like, will indicate different operating parameters.

As the distal, fixed diameter cutter assembly is rotated and advanced to remove occlusive material, fluid, debris, particulates, and the like are aspirated using primary and/or secondary aspiration mechanisms described above. It may be desirable to alternate between advancing and retracting (i.e. axially translating) dual cutter assembly 50 to facilitate the aspiration of particulates through ports 294, 304, 306, etc. in dual cutter assembly 50. Additionally, an enlarged cutter housing may be provided, as described above, for retracting cutter assembly 50 in a retrograde direction (i.e. proximally) within the cutter housing. During aspiration, this creates a laminar-like flow, thereby more effectively drawing fluid and particulates into the enlarged cutter housing and permitting particulates to be further broken down by the action of the rotating cutter assembly within housing 48. Larger particulates may thus be broken down to a size that can be withdrawn, with fluids, through aspiration ports 294, 304, 306, etc.

Figure 20A:
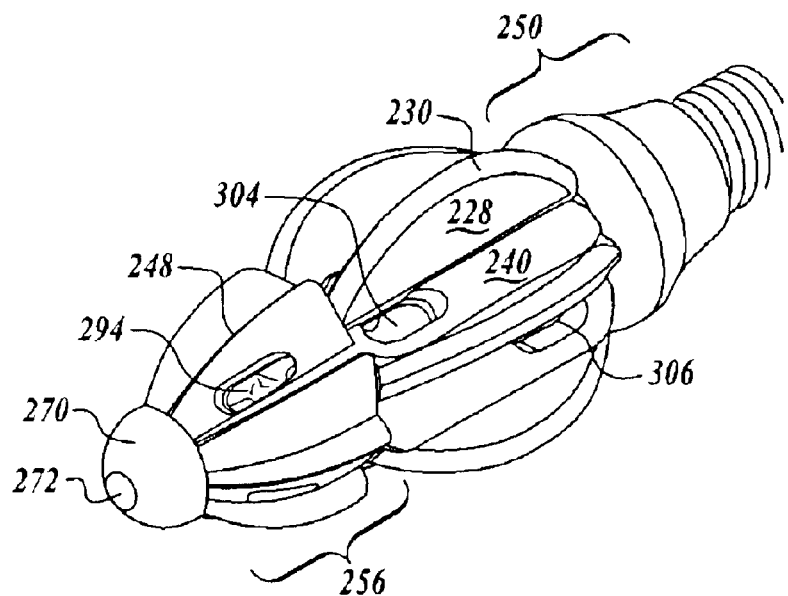
FIG. 20A illustrates an enlarged, perspective view of one embodiment of the dual cutter assembly of FIG. 19A with the cutter assembly in an expanded configuration.
Figure 20B:
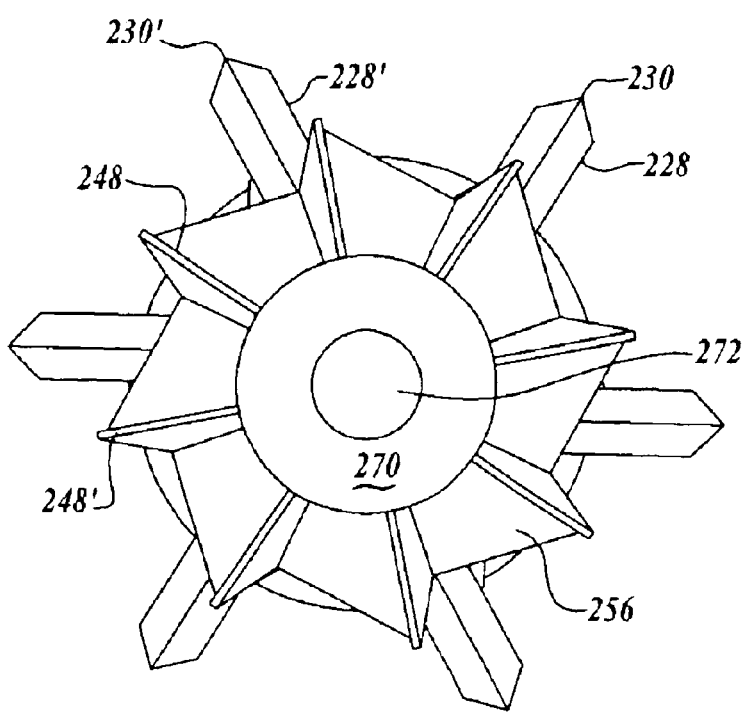
FIG. 20B illustrates an enlarged, front view of one embodiment of the dual cutter assembly of FIG. 20A with the cutter assembly in the expanded configuration.

When one or more initial pilot passes are complete, the dual cutter assembly may be retracted to a proximal boundary of the occlusion, and the direction of rotation of the expandable cutter assembly is reversed. Reversing the direction of rotation causes cutting members 254 of the variable diameter, expandable cutter assembly to open to an expanded configuration, as illustrated in FIGS. 20A and 20B. Specifically, as the dual cutter assembly 50 is rotated in one direction (e.g., clockwise), centrifugal forces of rotation combine with hydrodynamic and frictional forces between the surrounding fluid within the lumen and blades 228 of cutting members 254, causing cutting members 254 to pivot around the axis of rod sections 224. Cutting members 254 rotate freely within the first receiving apertures 220 and second receiving apertures 264 in proximal bushing 250 and distal cutter 256, respectively. Cutting members 254 rotate from a tangential orientation, in which blades 228 are in contact with the respective support faces 240 of raised spines 238 of central block 252 (i.e., the contracted configuration) to a radial orientation in which blades 228 of cutting members 254 are in contact with stop faces 242 of raised spines 238 of central block 252 (i.e., the expanded configuration). Stop faces 242 of raised spines 238 check the rotational movement of the cutting members 254, as well as provide support to blades 228 of cutting members 254 while in the larger diameter, expanded configuration during operation. Movement of the cutting members to the radial configuration increases the overall outer diameter of the cutter assembly. For example, in selected embodiments, the outer diameter of the expandable cutter assembly and the variable diameter cutter in the contracted configuration is approximately 2 mm, and the cutter assembly is expandable to a larger diameter of approximately 2.75 mm. As previously described, the present invention may be designed in a wide range of sizes to accommodate various applications, materials to be removed, lumens, and the like.

While in the expanded configuration, the expandable cutter assembly may be axially translated along guidewire 11 to retrace the pilot-pass made through the occlusion, whereupon beveled edges 230 of cutting members 254 engage the occlusive material, removing a larger volume of occlusive material. As previously described, aspiration is provided throughout the operation of the expandable cutter assembly to effectively remove the particulate debris dislodged during removal of the occlusive material.

After sufficient occlusive material has been removed, the expandable cutting assembly is contracted by rotating dual cutter assembly 50 in the smaller diameter direction, for the purpose of this example, in a clockwise direction. The centrifugal, hydrodynamic and frictional forces again act on blades 228 of cutting members 254, causing the cutting members to pivot about the axis of rod sections 224 of cutting members 254. Cutting members 254 thus move from a radial orientation, in which blades 228 are in contact with stop faces 242 of raised spines 238 of central block 252 (i.e., the expanded configuration) to a tangential position in which blades 228 are in contact with the respective support faces 240 of raised spines 238 of central block 252. Support faces 240 of raised spines 238 stop the rotational movement of the cutting members 254, as well as provide support to blades 228 of cutting members 254 while in the contracted, smaller diameter configuration. While in its contracted, smaller diameter condition, dual cutter assembly 50 may be retracted into a primary sheath or catheter for withdrawal from the material removal site or advanced along guidewire 11 to perform additional operations.

Figure 21:
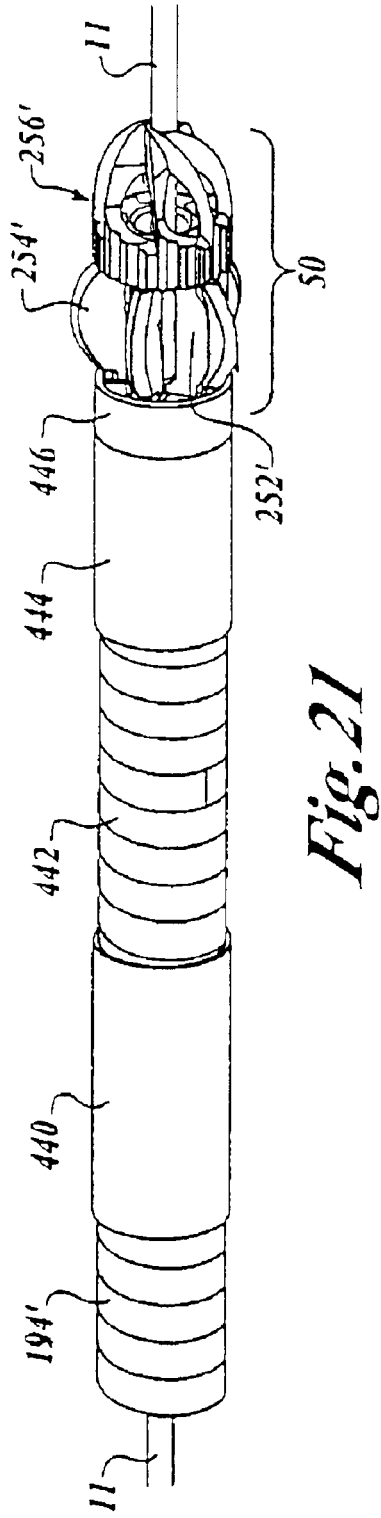
FIG. 21 illustrates an enlarged, perspective view of the distal end of a coiled metallic catheter with a dual cutter assembly in the expanded configuration.

FIGS. 21–27B illustrate additional preferred embodiments of the present invention. FIG. 21 illustrates an alternative embodiment of the present invention comprising at least one flexible conduit catheter 194', with drive shaft 25, preferably a multi-helical drive shaft, extending coaxially within its internal lumen. A proximal encasement 440 fixedly connects flexible conduit catheter 194' to a secondary segment of flexible conduit catheter 442, which in turn is fixedly connected to a distal encasement 444. Distal encasement 444 forms a slip-bearing fitting with a proximal cap 446, thereby permitting free rotation of drive shaft 25 and dual cutting assembly 50 within a coiled metallic catheter. As in previously described embodiments, dual cutting assembly 50 comprises a central block 252', a fixed diameter distal cutter 256' and a plurality of cutting members 254'.

Figure 22:
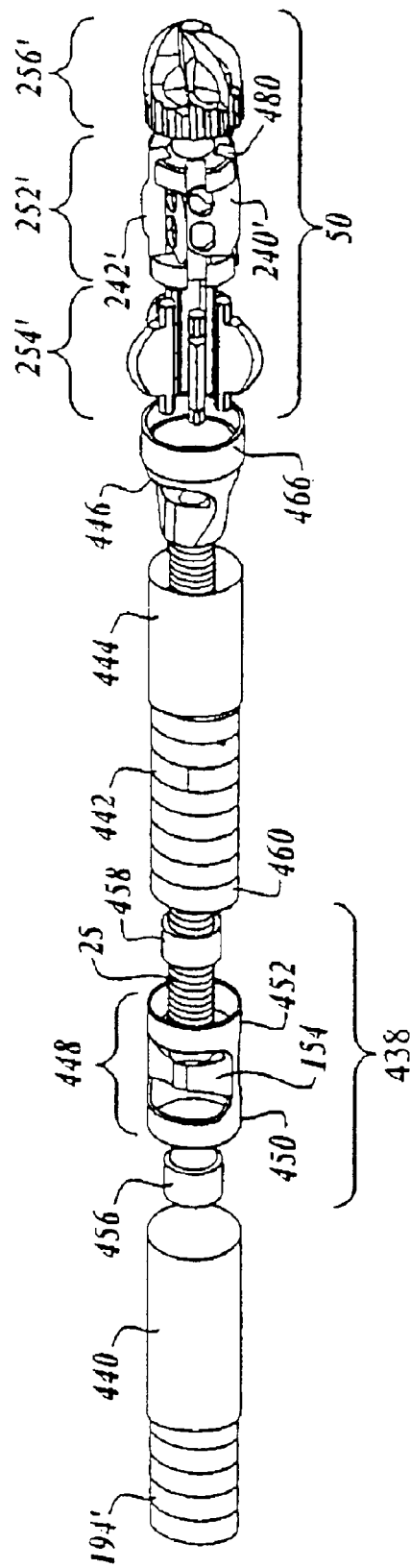
FIG. 22 illustrates an enlarged, perspective, exploded view of the cutter assembly of FIG. 21 and its relationship to a drive shaft and catheter.
Figure 23:
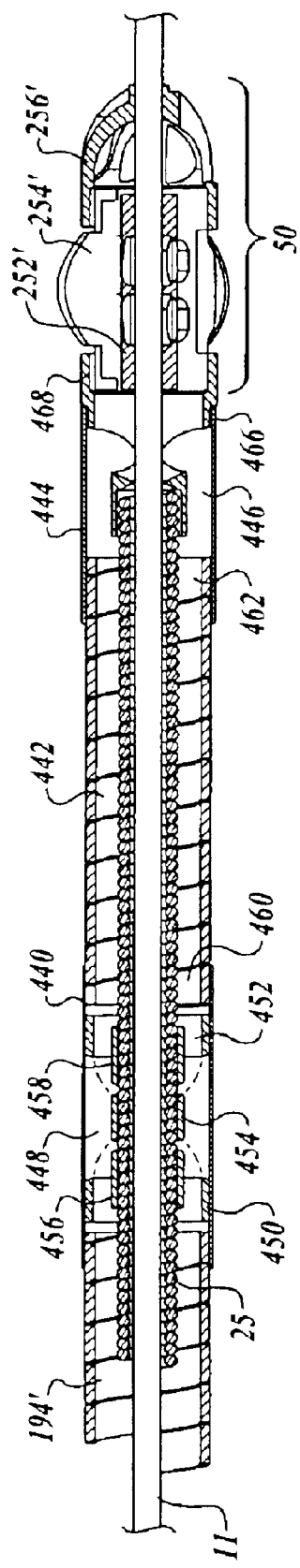
FIG. 23 shows a cross-sectional internal view of the cutter assembly shown in FIG. 21 and its relationship to a drive shaft and catheter.

As illustrated in FIGS. 22 and 23, drive shaft 25 may be provided with retainer assembly or mechanism 438 for interconnecting drive shaft 25 and flexible conduit catheter 194'. Any conventional assemblies or mechanisms may be utilized, such as a retainer 448 having a first end 450 fixedly connected to flexible conduit catheter 194' and a second end 452 fixedly connected to a first end 460 of secondary segment of flexible conduit catheter 442, by any conventional method such as by welding, laser-welding, soldering, brazing, adhesive bonds and the like. Retainer 448 works in conjunction with one or more thrust bearings to facilitate cooperative axial translation of drive shaft 25 and flexible conduit catheter 194' in either an antegrade or retrograde direction. A first thrust bearing 456 is fixedly connected to drive shaft 25 proximal to center section of retainer 454, and a second thrust bearing 458 is fixedly connected to drive shaft 25 distal to center section of retainer 454 in such a manner as to bring first 456 and second 458 thrust bearings in close or tight association with center section 454 of retainer 448. Drive shaft 25 freely rotates within central aperture of retainer 448. The retainer assembly may be enveloped by a tubular sheath, such as proximal encasement 440 to add additional strength and provide a relatively smooth profile for flexible conduit catheter 194'.

Notably, retainer assembly 438 and proximal encasement 440 are located an operable distance from cutter assembly 50. "Operable distance," as used herein, is defined as a distance which permits secondary segment of flexible conduit catheter 442 and associated cutter assembly 50 to retain sufficient flexibility to effectively maneuver within intralumenal spaces, particularly along curved, arched and/or branched sections of body lumens. The distance between retainer assembly 438/proximal encasement 440 and distal end of cutter assembly 50 may be from less than 1 cm to over 20 cm.

Cutter assembly 50 is fixedly connected to drive shaft 25 while permitting free rotation within flexible conduit catheter 194'. Drive shaft 25 is fixedly connected to a proximal cap 446, which has a distal flange section 466 fixedly connected central block 252'. This arrangement transfers rotational movement from drive shaft 25 to dual cutter assembly 50. Proximal cap 446 is provided with a central aperture for receiving guide wire 11, and a number of cut-away sections to create one or more accesses continuous with the lumen within all sections of flexible conduit catheter 442, 194'. This lumen serves as a conduit for aspiration and infusion materials and is continuous with the various ports of dual cutter assembly 50. A slip seal/bearing assembly 468 is created at the connection between distal encasement and flange section of proximal cap 466 thereby permitting free rotation of drive shaft 25, proximal cap 446 and dual cutter assembly 50 within flexible conduit catheter 194', 442 without imparting rotational movement to flexible conduit catheter 194', 442, which minimizes trauma to the surrounding tissues.

Figure 24:
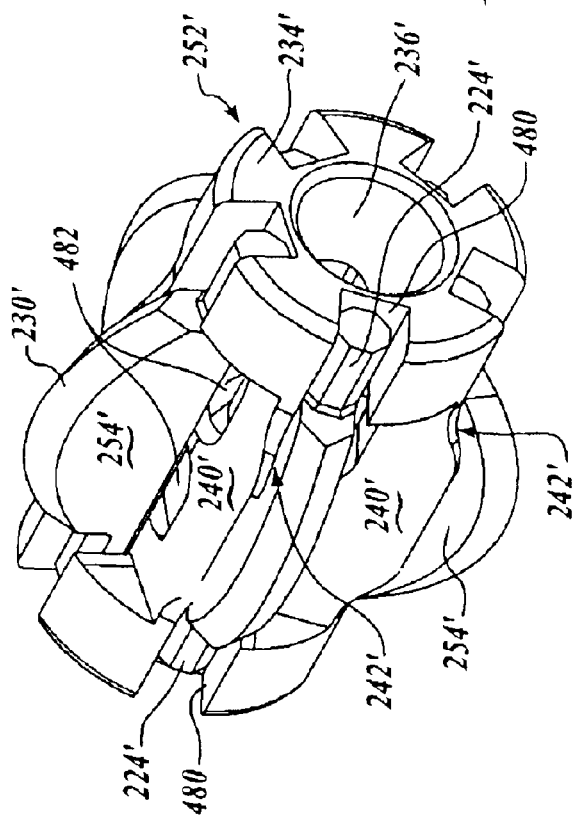
FIG. 24 shows an enlarged, perspective view of the expandable cutter shown in FIG. 21, highlighting the central block and cutting members assembly.
Figure 25A:
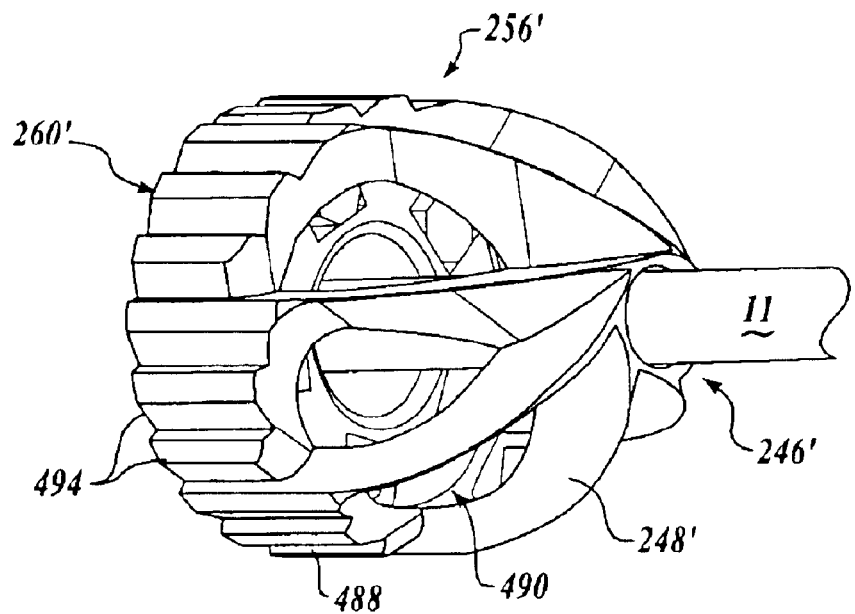
FIG. 25A illustrates an enlarged perspective view of another embodiment of the distal cutter shown in FIG. 21.
Figure 25B:
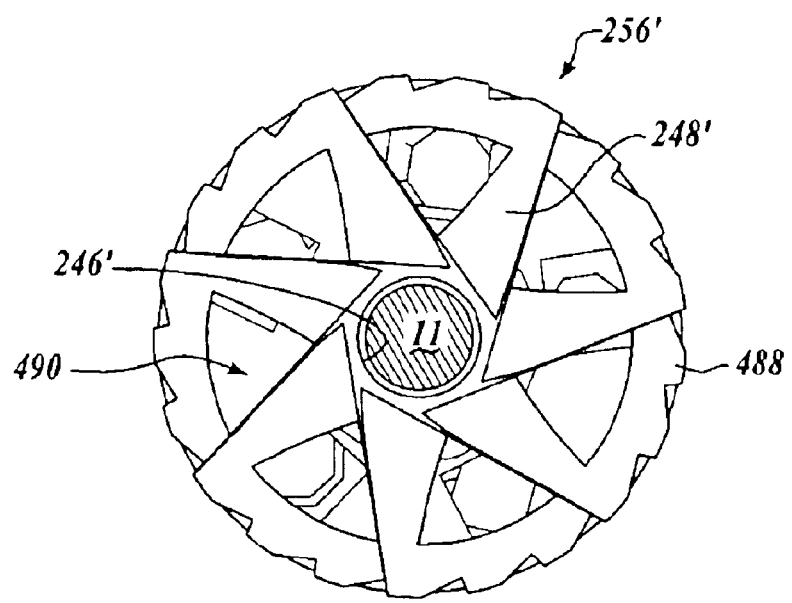
FIG. 25B shows a front view of the distal cutter of FIG. 25A.

As shown in FIGS. 22–24, central block 252' may be fitted with any suitable number of cutting members 254', such as eight (8) or fewer. The drawing shows a central block having five (5) cutting members but, depending upon the application and overall dimensions of the cutting assembly, greater or fewer than 5 cutting elements may be employed. FIG. 24 shows central block 252' having a plurality of receiving slots 480 for receiving rod sections 224' of cutting members 254'. Cutting members 254' may be formed from interconnected rod and blade members, or preferably machined as an integral piece. As disclosed above, cutting members 254' are provided with beveled edges 230', and operate according to the principles of differential cutting. It is understood that any suitable differential cutting angle may be utilized for beveled edge 230' in addition to those depicted in the figures. A central aperture 236' is provided running along the longitudinal axis of central block 252' to permit free axial translation of guide wire 11 and/or other components, as well to provide a conduit for aspiration and infusion. A plurality of ports 482 may be provided in central block 252' which are continuous with central aperture 236' and lumen of flexible conduit catheter 442, 194', further providing aspiration and/or infusion capabilities to dual cutter assembly 50. This particular embodiment provides a greater number of ports 482 in central block 252', thereby increasing aspiration and infusion efficiency.

Distal face 234' of central block 252' is fixedly connected to proximal face 260' of fixed diameter distal cutter 256' by any conventional method, such as by welding, preferably laser welding, soldering, brazing, adhesive bonds and the like. As more clearly illustrated in FIGS. 25A and 25B, distal cutter 256' is generally of tapered, oblong, conical or frustoconical design, or any suitably balanced configuration, and is provided with a plurality of raised "arch-like" cutting flutes or blades 248' radiating from central aperture 246' to body 488 of distal cutter 256'. This embodiment of a distal cutter also preferably operates according to the principal of differential cutting. Additionally, proximal and distal aspects of cutting flutes or blades 248' may be chamfered to render them atraumatic.

Distal cutter 256' may be provided with a plurality of port-like cutouts for aspiration and infusion. In the context of this particular embodiment, port-like cutouts may also be referred to as ports. Each pair of cutting flutes 248' is cut away to provide an aspiration cutout 490, which forms an internal cavity that is continuous with central aperture 236' of central block. This arrangement provides an aspiration and infusion conduit to the most distal end of dual cutter assembly 50. The design and arrangement of cutting flutes 248', and aspiration cutouts 490 create an open configuration providing substantially maximal cutout surface area, which allows a greater volume of material to be aspirated from the material removal site. Additionally, distal cutter 256' may have any sort of cutting and/or grinding elements 494 associated with body 488 of distal cutter 256' to further facilitate removal of occlusive material.

Figure 26A:
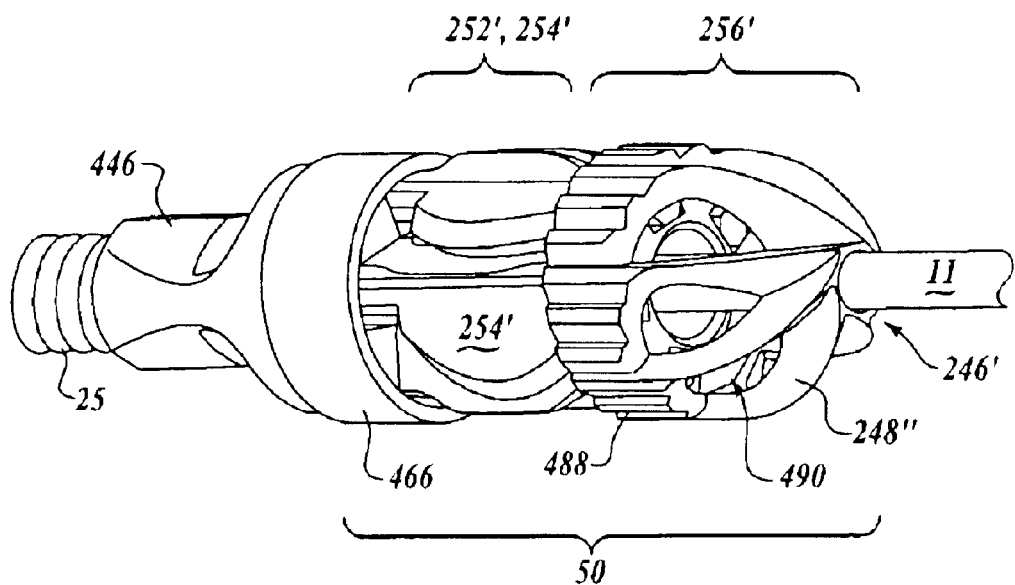
FIG. 26A shows the expandable cutting assembly shown in FIG. 21 in the contracted configuration.
Figure 26B:
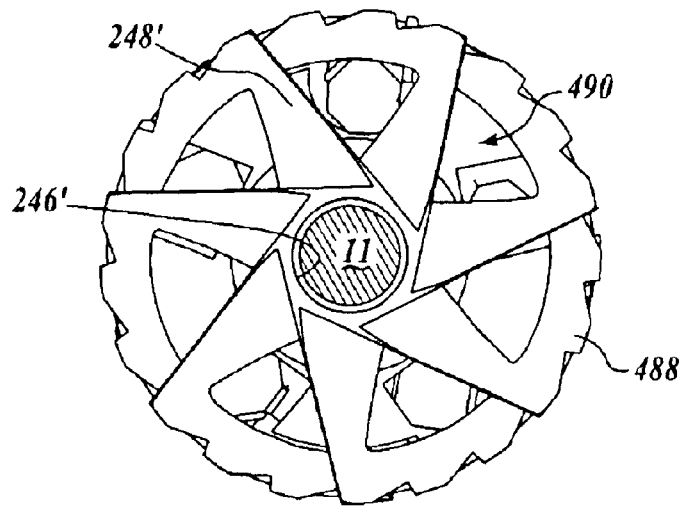
FIG. 26B provides a front perspective of the embodiment illustrated in FIG. 26A.
Figure 27A:
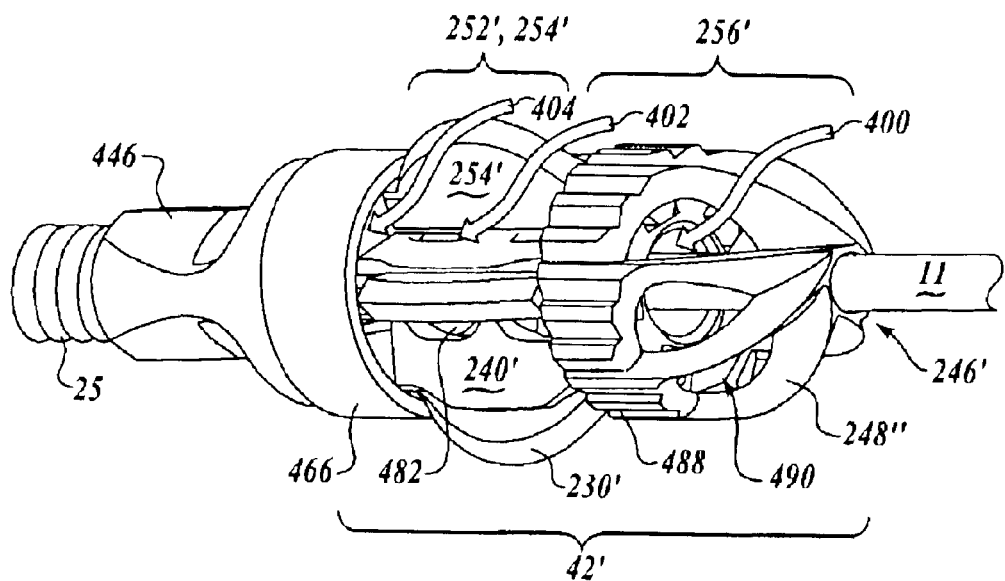
FIG. 27A shows the expandable cutting assembly shown in FIG. 21 in the expanded configuration.
Figure 27B:
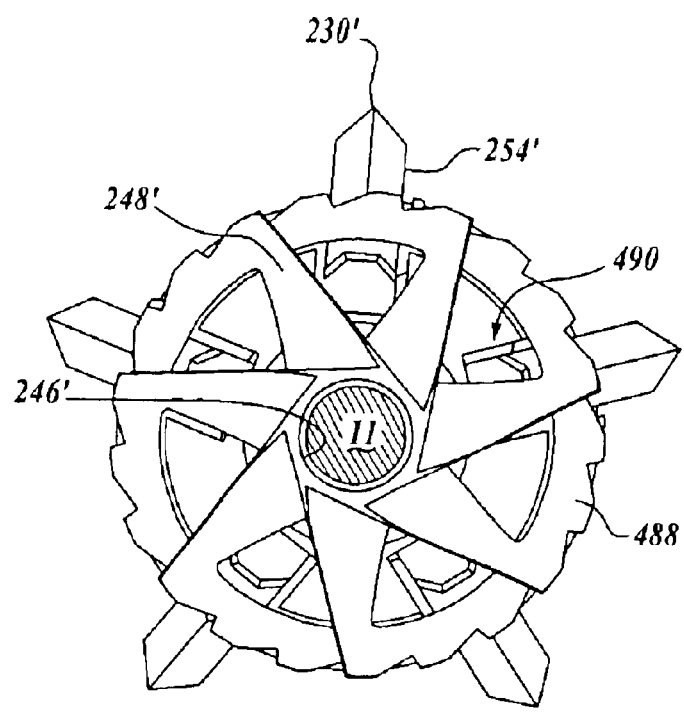
FIG. 27B provides a front perspective of the embodiment illustrated in FIG. 27A.

FIGS. 26A to 277B illustrate dual cutter assembly 50 in a contracted, smaller diameter condition (FIG. 26) and an expanded, larger diameter condition (FIG. 27). Cutting members 254' freely pivot within recesses 480 of central block 252' and depending on the direction of rotation, rotate from a tangential orientation, in which blade sections of cutting members engage respective support faces 240' (i.e., the smaller diameter, contracted configuration) to a radial orientation in which blade sections of cutting members 254' are in contact with stop faces 242' of central block 252' (i.e., the larger diameter, expanded configuration). Stop faces 242' check rotational movement of blade members and provide support while operating in the expanded configuration.

The general principles of operation described above apply to the embodiments illustrated depicted in FIGS. 21–27. Notably, this embodiment provides a fixed diameter distal cutter 256' having cutting flutes 248' that immediately engage occlusive material. Additionally, this embodiment provides a comparatively large aspiration conduit area by virtue of the large aspiration cutouts or ports 490. During aspiration, aspirate and particulates are drawn through aspiration cutouts, or ports 490 of distal cutter 256', ports 482 of central block 252', as well as spaces between central block 252' and proximal cap 466, as shown by arrows 400, 402 and 404, respectively.

According to preferred embodiments of the present invention, a temperature sensor is mounted in proximity to the site of material removal, preferably at the site where the cutter assembly engages the material to be removed. One or more temperature sensor(s) may be mounted, for example, to the cutter assembly and provide temperature data, via electrical or wireless communication, to the control unit.

In one embodiment, a thermocouple is bonded to a surface of a cutter and lead wires connected to the thermocouple are conveyed, in proximity to drive shaft 25, to control unit 25. Alternatively, lead wires may be woven into a metallic coil drive shaft 25. Lead wires are transitioned out of the advancer using rotating contacts. The thermocouple in this embodiment measures the temperature at the material removal site. This temperature data may be used in control features directly, or it may be related to the temperature at a lumen surface by empirical derivation. In another embodiment, fiber-optic based infra-red temperature monitoring of a lumen surface may be provided. Light wavelengths on the order of 1.4 microns transit blood and may be used, with suitable filtering and/or sensing means, to interrogate the surface of a lumen and measure its temperature during a material removal operation.

According to yet another embodiment, an optical dye-based fiber optic arrangement may be employed for temperature sensing. A temperature sensitive dye that has different optical transmissivity characteristics with changes in temperature may, for example, be released from a reservoir at the distal end of a fiber optic wire that is mounted, or embedded, in the cutter assembly. According to another embodiment, an integrated circuit diode junction may be mounted in or in proximity to a cutter assembly. An integrated circuit having an optical receiver and/or transmitter and/or amplifier may be used. Incorporating an amplifier in combination with a receiver and/or transmitter reduces noise from transmission of a weak signal over the length of the drive shaft and catheter.

Yet another embodiment may employ a bimetal strip as a temperature sensing means. Active or passive temperature monitoring may be provided, for example, at a catheter tip, using a bimetallic strip comprising two bonded metals having different coefficients of thermal expansion. A clutch means incorporating two metals having different coefficients of thermal expansion may additionally or alternatively be employed. A memory metal, such as nickel-titanium, having temperature sensitivity, may be used as a temperature monitor in addition to, or as an alternative to a bimetal strip. This embodiment may be employed for temperature monitoring or the cutter assembly, the lesion, and/or blood in the area of the material removal operation.

Finally, one or more thermistors that measure changes in electrical resistance that occur as a consequence of changes in temperature, may be employed for temperature monitoring at the material removal site according to the present invention. Additional and alternative temperature measurement devices are known in the art and may be adapted, according to the present invention, to provide temperature monitoring at a material removal site.

Another aspect of methods and systems of the present invention involves the implementation of certain automated and selectable control features. Thus, according to one embodiment, a material removal system of the present invention implements control features based on an operator's input of, or a sensed value for, specified parameters. Specified parameters may include, for example: lesion length, lesion type and character, such as calcified, fibrotic, lipid/fatty, and the like; and/or historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. One or any combination of these parameters may be input by an operator, or sensed at a material removal site, and communicated to a control unit comprising, for example, a programmable logic controller. The control unit may determine a recommended treatment operation based, for example, on the lesion length, lesion type, rate and volume of blood flow, percentage lumen restriction and lumen diameter. The recommended treatment may specify the cutter assembly size and type, the rotation rate and/or rotation profile of the cutter, the advance rate and/or the advance profile, the aspiration rate and/or profile, the infusion rate and/or profile, and the like. The treatment recommendation may be provided on a display screen, for example, provided as part of the control unit.

The treatment recommendation may then be implemented by an operator, with specified and predetermined treatment parameters automated by the control unit. Based on the specified parameters input by the operator or sensed at a material removal site, an automated cutter assembly control unit may determine the recommended treatment, as described above. Implementation of the recommended treatment may be accomplished by an operator, or by providing automated operating conditions, such as cutter assembly rotation rate and profile, cutter assembly advance rate and profile, aspiration rate and profile, infusion rate and profile, and the like. Material removal systems of the present invention that provide automated operating features preferably provide operator selection and actuation of the automated features, in combination with an operator override function, whereby the operator may manually control certain operational parameters, whereas selected operational parameters may be automated.

Yet another aspect of methods and systems of the present invention involves providing a catheter with a low pressure occluding balloon at its distal tip. This device is particularly useful in removing materials from a carotid artery lesion using an atherectomy device of the present invention having a high rate of aspiration flow. In one embodiment, a sheath or guiding catheter is slidably disposed over the catheter, said sheath or guiding catheter having a low pressure occluding balloon at the distal tip positioned proximal to a cutter assembly, such that the balloon can be temporarily inflated to block antegrade blood flow proximal to the cutter assembly while the cutter assembly is advanced, and cuts and aspirates. Once the antegrade blood flow is stopped, the flow created by the aspiration of the catheter pulls make-up blood retrograde, the source of such blood being provided by the connection of the distal cerebral arteries to the other side of the brain and the contralateral carotid artery via the Circle of Willis. Collateral circulation through blood vessels in the brain may thus be reversed. This creates flow towards the cutter assembly, as opposed to away from it, thereby preventing embolic material from moving distally and potentially causing a blockage of the smaller arteries of the brain. Use of the low pressure occluding balloon thus prevents embolization at the site of material removal, precludes the need for a distal protection device, and provides continuous perfusion of the brain, even while blood flow is retrograde in the treated artery.

It will be understood that the foregoing disclosures are merely illustrative of the invention and its principles. Modifications and variations in the details of the disclosure will be evident to those skilled in the art to which this invention relates and these modifications are intended to be within the scope and principles of the appended claims.

We claim:

1. An intralumenal material removal device comprising a rotatable cutter assembly in communication with a drive shaft for receiving rotational torque from the drive shaft, the cutter assembly comprising an adjustable diameter cutter having a plurality of rotatable, fan-shaped cutting blades, wherein each of the cutting blades has a beveled edge for cutting, and wherein each of the cutting blades is individually rotatable around its own axis of rotation between a smaller diameter tangential orientation and a larger diameter radial orientation, and wherein each axis is circumferentially spaced around a central longitudinal axis.

2. The device of claim 1, wherein the adjustable diameter cutter has a plurality of material removal ports in communication with a lumen, wherein the material removal ports are located between the cutting blades and the material removal ports permit flow through when the adjustable diameter cutter is expanded.

3. The device of claim 1, wherein the cutter assembly further comprises a fixed diameter cutter having a plurality of fixed cutting blades.

4. The device of claim 3, wherein the cutting blades of the fixed diameter cutter have beveled edges and operate using the principle of differential cutting.

5. The device of claim 1, further including a plurality of stop faces that contact the cutting blades when the cutting blades are in a smaller diameter condition.

6. The device of claim 1, further including a plurality of support faces that contact the cutting blades when the cutting blades are in a larger diameter condition.

7. The device of claim 3, wherein the fixed diameter cutter is positioned distally from the adjustable diameter cutter.

8. The device of claim 7, wherein the fixed diameter cutter has a frusto-conical cross-sectional configuration and a series of raised cutting flutes.

9. The device of claim 1, wherein the blades are rotatable between the tangential and radial orientations by changing direction of rotation of the cutter assembly.

10. An intralumenal material removal device comprising: a rotatable cutter assembly operably coupled to a distal end of a rotatable drive shaft, the cutter assembly comprising an expandable diameter cutter having a plurality of blades, each of the blades mounted for pivoting between a tangential orientation and a radial orientation without causing the blades to flex.

11. The device of claim 10, wherein the cutting blades of the expandable diameter cutter operate using the principle of differential cutting.

12. The device of claim 10, wherein the expandable diameter cutter has a plurality of material removal ports in communication with a lumen, wherein the material removal ports are located between the cutting blades and permit flow through when the cutting blades are positioned in a radial orientation.

13. The device of claim 10, further including a plurality of stop faces that contact the cutting blades when the cutting blades are positioned in a radial orientation.

14. The device of claim 13, further including a plurality of support faces that contact the cutting blades when the cutting blades are in a retracted position.

15. The device of claim 1 or 10, additionally comprising a temperature sensor mounted on or in proximity to the rotatable cutter assembly.

16. The device of claim 1 or 10, wherein the drive shaft is a non-compressible multi-filar metallic coil.

17. The device of claim 1 or 10, additionally comprising a magnetic coupler assembly mounted to the drive shaft at its proximal end to provide detachable coupling of the drive shaft to a drive train.

18. The device of claim 1 or 10, wherein the drive shaft comprises a helical coil having a polymer layer sealing an outer and/or inner surface of the drive shaft.

19. The device of claim 18, wherein the polymer layer comprises polytetrafluoroethylene (PFTE).

20. The device of claim 1 or 10, wherein the cutting blades are arranged in a radially symmetrical configuration.

21. The device of claim 1 or 10, additionally comprising a bearing assembly coupling the cutter assembly to a conduit catheter, whereby the cutter assembly rotates freely around a central axis and a fluid-tight junction is formed between the conduit catheter and the cutter assembly.

22. The device of claim 1 or 10, wherein the cutting blades are constructed from a material selected from the group consisting of: metals, metal alloys and ceramics.

23. The device of claim 1 or 10, wherein the cutting blades are constructed from a material selected from the group consisting of: series 300 vanadium steel; series 400 vanadium steel; nickel-titanium; titanium; titanium-containing metals; oxide ceramics; and combinations thereof.

24. The device of claim 1 or 11, wherein the beveled edges are sharpened.

25. The device of claim 1 or 10, wherein the cutting blades comprise blade sections mounted on rods that are pivotably seated on a central block.

26. The device of claim 1 or 10, wherein the cutter assembly has a central lumen.

27. The device of claim 26, additionally comprising a plurality of circumferentially interspaced ports communicating with the lumen.

* * * * *